US010186163B1

(12) United States Patent
Letterese et al.

(10) Patent No.: US 10,186,163 B1
(45) Date of Patent: Jan. 22, 2019

(54) SYSTEM AND METHOD FOR REDUCING STRESS AND/OR PAIN

(71) Applicants: Peter D. Letterese, Weston, FL (US); Thomas J. Karas, St. Clair Shores, MI (US)

(72) Inventors: Peter D. Letterese, Weston, FL (US); Thomas J. Karas, St. Clair Shores, MI (US)

( * ) Notice: Subject to any disclaimer, the term of this patent is extended or adjusted under 35 U.S.C. 154(b) by 0 days.

(21) Appl. No.: 15/620,564

(22) Filed: Jun. 12, 2017

Related U.S. Application Data

(63) Continuation-in-part of application No. 14/483,053, filed on Sep. 10, 2014, now abandoned, which is a
(Continued)

(51) Int. Cl.
*G09B 1/38* (2006.01)
*G09B 7/02* (2006.01)
(Continued)

(52) U.S. Cl.
CPC .............. *G09B 7/02* (2013.01); *A61B 5/165* (2013.01); *A61B 5/742* (2013.01);
(Continued)

(58) Field of Classification Search
CPC ....................................................... G09B 1/38
(Continued)

(56) References Cited

U.S. PATENT DOCUMENTS 2,727,510 A    12/1955   Thompson
2,966,747 A *   1/1961   Johnson ................. G09B 19/02
                                                           434/199
(Continued)

FOREIGN PATENT DOCUMENTS

EP            2397957 A1    12/2011

OTHER PUBLICATIONS

Chris Harris; The Complete Idiots Guide to Self Defense; Alpha Books; 2000; six (6) pages.
(Continued)

*Primary Examiner* — John E Simms, Jr.
*Assistant Examiner* — Dolores Collins
(74) *Attorney, Agent, or Firm* — Diederiks & Whitelaw, PLC

(57) ABSTRACT

A stress reduction and/or pain reduction method and system, includes measuring an initial level of user stress, which level is unacceptable, having the user hold a card having multiple single digit math problems therein, the problems being in multiple series of four problems, the math problems comprising at least one of addition, subtraction, and multiplication problems, displaying to and instructing the user to complete a first series of four and only four problems correctly, displaying to and instructing the user to complete a second series of four and only four problems incorrectly, again measuring the user's stress level and repeating the steps of displaying and instructing, and measuring, until the output from the device is acceptable. The same process may be followed using a camera or video camera and analyzing the image(s) for a Duchenne smile, in place of or in addition to measuring the indicator of stress.

11 Claims, 25 Drawing Sheets

Related U.S. Application Data continuation-in-part of application No. 12/954,531, filed on Nov. 24, 2010, now abandoned.

(60) Provisional application No. 62/349,814, filed on Jun. 14, 2016, provisional application No. 61/894,750, filed on Oct. 23, 2013, provisional application No. 61/881,682, filed on Sep. 24, 2013, provisional application No. 61/283,069, filed on Nov. 25, 2009.

(51) Int. Cl.
| | | |
|---|---|---|
| *G09B 19/00* | | (2006.01) |
| *G09B 5/02* | | (2006.01) |
| *A61B 5/16* | | (2006.01) |
| *A61B 5/00* | | (2006.01) |
| *G06K 9/00* | | (2006.01) |
| *A61B 5/024* | | (2006.01) |
| *A61B 5/021* | | (2006.01) |

(52) U.S. Cl.
CPC ..... *G06K 9/00255* (2013.01); *G06K 9/00302* (2013.01); *G09B 5/02* (2013.01); *G09B 19/00* (2013.01); *A61B 5/021* (2013.01); *A61B 5/024* (2013.01); *A61B 5/02405* (2013.01)

(58) Field of Classification Search
USPC .................................................. 434/191, 190
See application file for complete search history.

(56) References Cited

U.S. PATENT DOCUMENTS

| | | | |
|---|---|---|---|
| 3,154,070 A | 10/1964 | Meckelburg | |
| 3,272,198 A | 9/1966 | Balkin | |
| 3,345,759 A * | 10/1967 | Harris .................... | G09B 19/02 273/294 |
| 4,043,324 A | 8/1977 | Shaw, IV | |
| 4,219,800 A | 8/1980 | LeViness | |
| 4,388,918 A | 6/1983 | Filley | |
| 4,583,952 A * | 4/1986 | De La Paz Rios .... | G09B 19/02 434/191 |
| 4,812,036 A | 3/1989 | Inoue | |
| 4,894,777 A | 1/1990 | Negishi | |
| 4,928,704 A | 5/1990 | Hardt | |
| 5,064,410 A | 11/1991 | Frenkel et al. | |
| 5,304,112 A | 4/1994 | Mrklas et al. | |
| 5,323,783 A | 6/1994 | Henkin et al. | |
| 5,377,100 A * | 12/1994 | Pope .................... | A61B 5/0476 341/20 |
| 5,465,729 A | 11/1995 | Bittman et al. | |
| 5,571,020 A | 11/1996 | Troudet | |
| 5,594,530 A | 1/1997 | Masuda et al. | |
| 5,870,731 A * | 2/1999 | Trif ........................ | G06N 5/048 434/118 |
| 5,940,798 A | 8/1999 | Houde | |
| 5,944,530 A * | 8/1999 | Ho ........................... | G09B 5/06 434/236 |
| 6,007,569 A | 12/1999 | Frenkel et al. | |
| 6,102,846 A | 8/2000 | Patton et al. | |
| 6,159,506 A | 12/2000 | Bieser et al. | |
| 6,457,975 B1 | 10/2002 | Miranda et al. | |
| 6,484,062 B1 | 11/2002 | Kim | |
| 6,527,700 B1 | 3/2003 | Manico et al. | |
| 6,702,720 B2 | 3/2004 | Dardik | |
| 7,160,253 B2 * | 1/2007 | Nissila ................ | A61B 5/0006 600/26 |
| 7,226,792 B2 | 6/2007 | Roberts et al. | |
| 7,542,932 B2 | 6/2009 | Chalermkraivuth et al. | |
| 7,769,550 B2 | 10/2010 | Hyodo et al. | |
| 7,892,178 B1 * | 2/2011 | Bady .................... | A61B 5/0205 463/36 |
| 7,972,134 B2 | 7/2011 | Lai et al. | |
| 7,975,543 B2 | 7/2011 | Clem et al. | |
| 8,021,159 B1 | 9/2011 | Siegel | |
| 8,523,573 B1 * | 9/2013 | Villarreal-Reyes .... | G09B 19/22 434/129 |
| 8,529,457 B2 | 9/2013 | Devot et al. | |
| 8,556,939 B2 * | 10/2013 | Henderson ......... | A61B 17/7055 600/594 |
| 8,605,152 B2 | 12/2013 | Mills | |
| 8,617,044 B2 | 12/2013 | Pelgrim et al. | |
| 8,734,158 B2 * | 5/2014 | Cornell .................. | G09B 17/00 434/188 |
| 9,028,258 B2 | 5/2015 | Burdea | |
| 9,179,855 B2 | 11/2015 | Burdea et al. | |
| 9,278,278 B1 * | 3/2016 | Villarreal-Reyes ....... | A63F 1/00 |
| 2005/0065452 A1 * | 3/2005 | Thompson ............ | A61B 5/162 600/558 |
| 2005/0096396 A1 | 5/2005 | Davis et al. | |
| 2005/0181071 A1 | 8/2005 | Binder | |
| 2006/0058856 A1 | 3/2006 | Morrell | |
| 2007/0139362 A1 | 6/2007 | Colton | |
| 2008/0004550 A1 * | 1/2008 | Einav .................... | A61B 34/30 601/33 |
| 2008/0214944 A1 | 9/2008 | Morris et al. | |
| 2009/0082616 A1 | 3/2009 | Selig | |
| 2009/0124865 A1 * | 5/2009 | Kiernan ................ | A61H 37/00 600/300 |
| 2009/0131225 A1 * | 5/2009 | Burdea .................. | A63B 21/06 482/5 |
| 2009/0142738 A1 | 6/2009 | Suganuma | |
| 2009/0192402 A1 | 7/2009 | Corn | |
| 2009/0255543 A1 | 10/2009 | Oyama | |
| 2009/0271701 A1 | 10/2009 | Bossmeyer et al. | |
| 2010/0021873 A1 | 1/2010 | Stut et al. | |
| 2010/0153453 A1 | 6/2010 | Knowles | |
| 2010/0196860 A1 | 8/2010 | Donzow | |
| 2010/0292545 A1 * | 11/2010 | Berka .................... | A61B 5/048 600/301 |
| 2011/0112441 A1 * | 5/2011 | Burdea .................. | A63B 21/06 600/595 |
| 2011/0169927 A1 | 7/2011 | Mages et al. | |
| 2011/0232214 A1 * | 9/2011 | Lin ..................... | E04F 11/0201 52/188 |
| 2012/0136274 A1 * | 5/2012 | Burdea ............. | A61B 5/04842 600/545 |
| 2013/0180532 A1 | 7/2013 | Montaillier | |
| 2016/0166197 A1 | 6/2016 | Venkatraman et al. | |

OTHER PUBLICATIONS

Author Unknown; Centering Gaining Control Before a Performance; MindTools.com; four (4) pages.

Author Unknown; When 2 + 2 = Major Anxiety: Math Performance in Stressful Situations; ScienceDaily; Dec. 10, 2008; three (3) pages.

Author Unknown; Brain Challenge vol. 2: Stress Management; Gameloft.com; Dec. 30, 2013; six (6) pages.

* cited by examiner

SYSTEM AND METHOD FOR REDUCING STRESS AND/OR PAIN

CROSS REFERENCE TO RELATED PATENTS AND APPLICATIONS

This application claims priority from:
U.S. Provisional Patent Application Ser. No. 62/349,814, filed Jun. 14, 2016
U.S. Utility patent application Ser. No. 14/483,053, filed Sep. 10, 2014;
U.S. Provisional Patent Application Ser. No. 61/894,750, filed Oct. 23, 2013;
U.S. Provisional Patent Application Ser. No. 61/881,682, filed Sep. 24, 2013;
U.S. Utility patent application Ser. No. 12/954,531, filed Nov. 24, 2010; and
U.S. Provisional Patent Application Ser. No. 61/283,069, filed Nov. 25, 2009,
each and all of which applications are incorporated by reference herein.

BACKGROUND OF THE INVENTION

The present invention relates to a system and method for improving cognitive[1] and autonomic[2] brain functions, and also to a system and method for reducing stress and/or pain.

[1] Cognitive . . . of or pertaining to the mental processes of perception, memory, judgment, and reasoning, as contrasted with emotional and volitional processes.
[2] Autonomic (System) . . . system of nerves and ganglia (dense cluster of nerve cells) that innervates the blood vessels, heart, smooth muscles, viscera, and glands and controls their involuntary functions.

Medical research has shown that stress has an adverse effect on health, and sometimes very adverse. For example, stress by definition raises a person's blood pressure, and for those with hypertension, stress can make blood pressure dangerously high. Hypertension can increase the risk of a heart attack or stroke up to three or four times. Stress, raises heart rate. Stress also makes it hard to focus, and so can result in bad decisions at critical moments, a freeze-response and/or a fight/flight response. Further, teachers and others have struggled for ages to try to make students and others smarter and/or learn more and/or do better in school and/or other intellectual endeavors. A mind which is clear of rumination and/or stress can put one in a better condition to learn.

SUMMARY OF THE INVENTION

Through trial and error, the inventors have found that it is important to carry out the method and system by displaying a first set of four problems of single digit simple mathematics to a user and instructing the user to do four problems (no more and no less) while holding a card and trying to answer correctly, followed by displaying a second set of problems and instructing the user to answer them incorrectly. These specific steps as well as others such as using a device providing an output indicative of the user's stress level takes the invention outside the realm of abstract idea or mental steps, particularly in combination with the use of the method and system until one has a "Duchenne" smile (defined herein). The Duchenne smile is determined by using a camera or video to view the user's face and determine if there is a Duchenne smile. The method and system may also be carried out using the same steps, except to monitor when the output indicative of stress reaches an acceptable predetermined level or reduction from the initial level. In addition, the stress indicator and the Duchenne smile monitoring methods may be combined by continuing until the Duchenne smile is reached and/or until the acceptable predetermined level or reduction.

In the system and method, the presence of physiological changes in response to this unique set of steps, like a unique algorithm that is computer-implemented, is patentable and is not an abstract idea or mere mental steps.

U.S. Pat. No. 5,870,731 to Trif et al discloses an adaptive problem solving method and system implemented on a computer. It is the novelty of the method that makes this invention patentable, not the addition of a computer for carrying out the method.

Similarly, U.S. Pat. No. 5,944,530 on a learning method and system that consider a student's concentration level includes a step of monitoring a student's concentration-sensitive behavior.

The method and system is a verifiable and observable, practical application of natural brain function; wherein a user is instructed what to do to activate at will the interactions of specific areas of the brain (see below for specifics), and in so doing, brings about cognitive and autonomic improvements with respect to the negative effects of Uncontrollable Stress. In accordance with one embodiment, a brain function improvement method and system, which is targeted to include a Stress Conversion (from Uncontrollable Stress to Controllable Stress) method and system, includes a Card or page having multiple columns and/or rows of math problems. There are four columns of eleven problems each. The math problems are simple arithmetic problems such as addition, subtraction and multiplication of single-digit numbers. They are never division. In fact, it is necessary that the problems be simple arithmetic problems such as addition, subtraction and multiplication, and not division.

In another application or as part of the above inventive methods and systems, a user who at any given time in the course of normal life becomes unhappy or (recurrently) afraid or anxious or worried, etc. is instructed to learn to pay attention to rather than ignore the fear, worry or anxiety, etc. The user then selects any four (4) problems in any a column or row of problems, or at their choice from any number of columns, or in any order and does those problems either silently or out loud. (In a preferred embodiment it does not matter whether the user answers the problem correctly.) Then he or she checks for the existence of the stress, etc. (or tries to). If the anxiety and/or stressed feeling and/or unhappiness and/or otherwise impeded brain function is gone completely, accompanied by a genuine, natural smile[3], the user is instructed to stop. If no genuine, natural (Duchenne) smile occurs, then he or she does another four (4) math problems, in any order, from either side of the Card, or both sides. The user then continues this same process until the stress, etc. is gone, the sole and singular evidence of which will be a genuine, natural (Duchenne) smile.

[3] Smile (as used in this application . . . refers specifically to a "Duchenne Smile" (a true natural smile involving muscles around the eye and is, named after its primary researcher amid-19th century French neurologist Guillaume Duchenne). Smiling, in which (in addition to using the zygomatic major muscle to raise the corners of the mouth), the orbicularis oculi muscle around the eye contracts, raising the cheeks high is uniquely associated with positive emotion.

The invention may also be embodied within a "Stress Conversion (from Uncontrollable Stress to Controllable Stress) Kit" preferably including the Card and instructions or the like, and overlaid on objects found in the home or at any and all types or places of employment or education, each containing a suggested set of single-digit math problems on each side. The Card could be done as an 8½×11 inch sheet, A4 sheet or other size. Card sizes of about 2"×4" or up to about 3½×5", 3"×6" or 3"×4" or sizes in between, are preferred due to the convenience of being about wallet sized. The Card is typically shaped as a book mark, and most preferably is 2½"×5½", plus or minus ½" in length.

There are many other embodiments. For example, the Card or paper may be in the form of a sticker, or may be directly imprinted onto an object, or may be a placard. Where the object is clothing or other fabric, the contents of the Card may be stitched onto the clothing or fabric. The Card in one of several forms, may thus be provided on furniture, and/or a vehicle dashboard (In all cases involving a vehicle containing any version of an embodiment of the invention is to be accompanied by a warning to the driver/operator never to read from or use the Card while the vehicle is in motion and/or requiring the operator's full attention while driving/operating the vehicle.) The Card in one of several other forms may thus be provided on a crib, clothing, a computer keyboard, a stroller, a machine or its control panel, furniture such as a desk, an appliance, a briefcase, and/or even a wall, and/or other objects or things where Stress Conversion (from Uncontrollable Stress to Controllable Stress) may be helpful, such as a hospital bed or doctor's office waiting room wall or chair or table.

In a most preferred embodiment, the user holds the Card or other physical item on which the math problems and instructions are located.

In a variation of the embodiments, there is a step or steps of monitoring blood pressure and/or heart rate. In further embodiments, people who have their minds preoccupied and/or are under stress and/or are nervous and/or in other normal and typical states of mind can be made "smarter" (i.e., can experience increased ability to think, analyze, communicate, learn, and comprehend), when following a method in accordance with such embodiments.

In the description below, various material that is protected by trademark and/or copyright is discussed for purposes of illustration, and such material is proprietary. No license or rights to use such protected material is granted herein. For example, "TheTRUSTCard" is a registered trademark. The instructions discussed herein will be equally effective if they merely substitute the word "Card" (or the equivalent) for the registered mark "TheTRUSTCard."

DESCRIPTION OF THE PREFERRED EMBODIMENT(S)

I. Exemplary Card Systems

Figure 1:
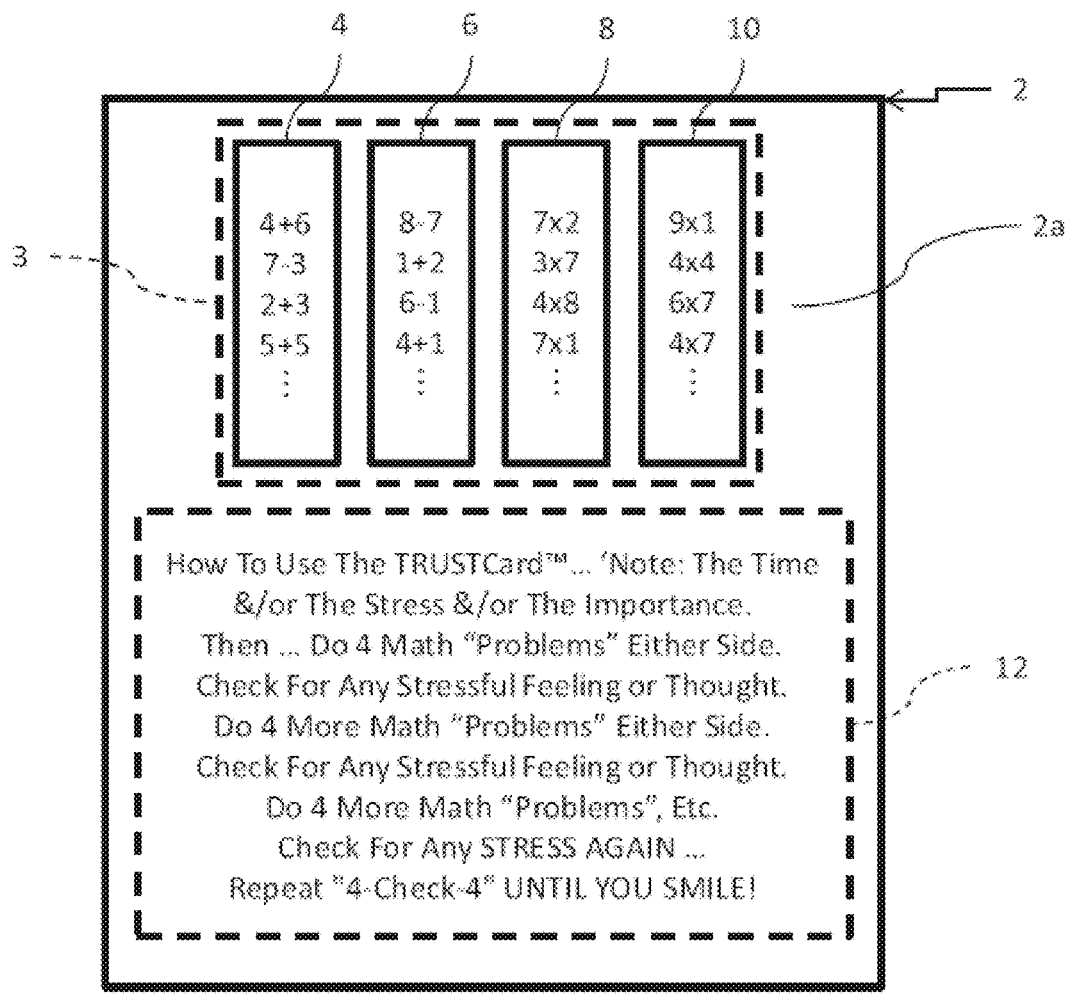
FIG. 1 is a drawing of one side of a math Card.

FIG. 1 shows a Card 2 embodying a stress conversion (from Uncontrollable Stress to Controllable Stress) system. The Card has a set of math problems arranged in aligned rows and columns. Card 2 has four columns 4, 6, 8, 10 of math problems in a math problem section 3. There also is preferably a set of instructions 12 on the Card.

The lines of math problems, which lines are straight, contain necessarily single digit math problems, such as single digit addition, multiplication and/or subtraction. Single digit division is not used. None of the problems require paper.

In a row or column, or in the whole set, the problems are addition, subtraction and/or multiplication.

Figure 2:
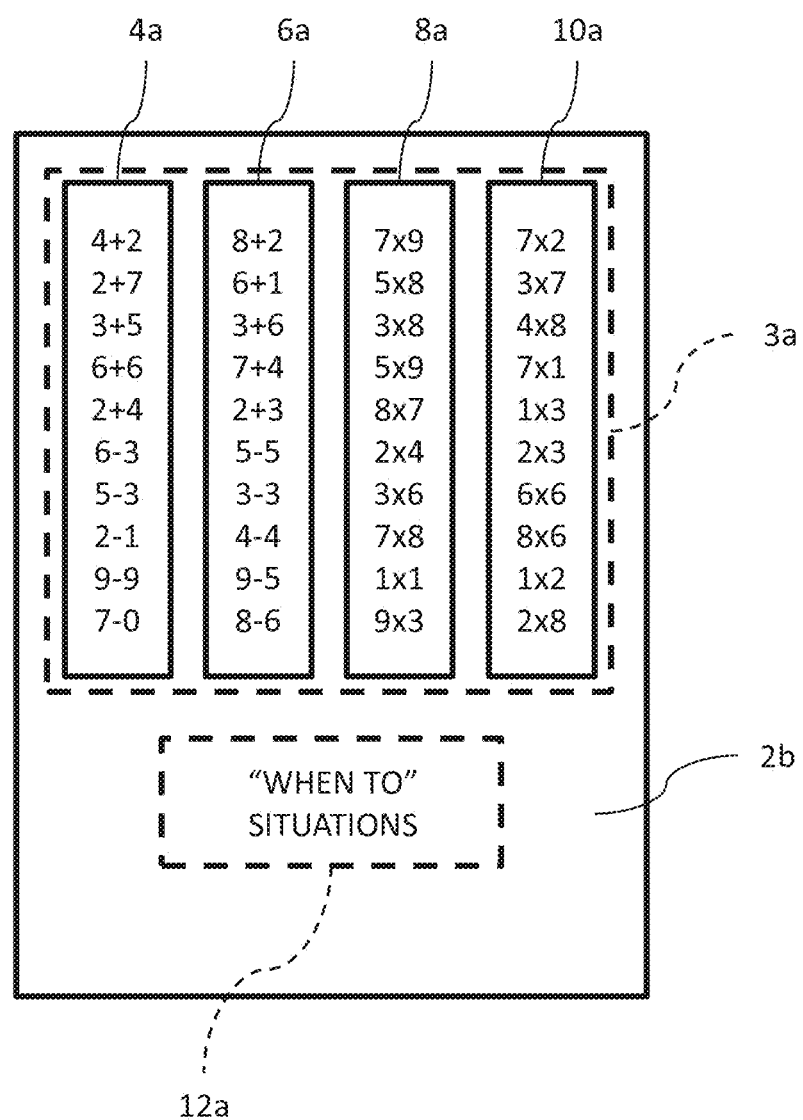
FIG. 2 is a drawing of a second side of a math Card.

FIG. 1 shows a front side 2a of a Card 2, and FIG. 2 shows a rear 2b thereof. The rear side will have instructions 12a. It also has four lines (columns) 4a, 6a, 8a, 10a each containing a number (such as ten) math problems in math problem section 3a. In this embodiment, there are addition and subtraction problems mixed together.

Instruction box 12 on the Card may say what is shown in FIG. 1, or may say in one form or another:

Here's How:
REMEMBER Anything STRESSFUL!
DO 4 Math "Problems"—Either Side
Try (if you can) to FEEL THAT STRESS AGAIN . . .
Do 4 More Math "Problems," Etc.
Try (if you can) to FEEL THAT STRESS AGAIN, Etc.
Stop IF/WHEN YOU FIND YOURSELF NATURALLY (DUCHENNE) SMILING!

A copyright notice should also appear on the Card, which Card is subject to copyright protection. There are also preferably a list of situations in which to use the car in "when to" section 12a on the rear of the Card.

II. Exemplary Card Methods

Figure 3:
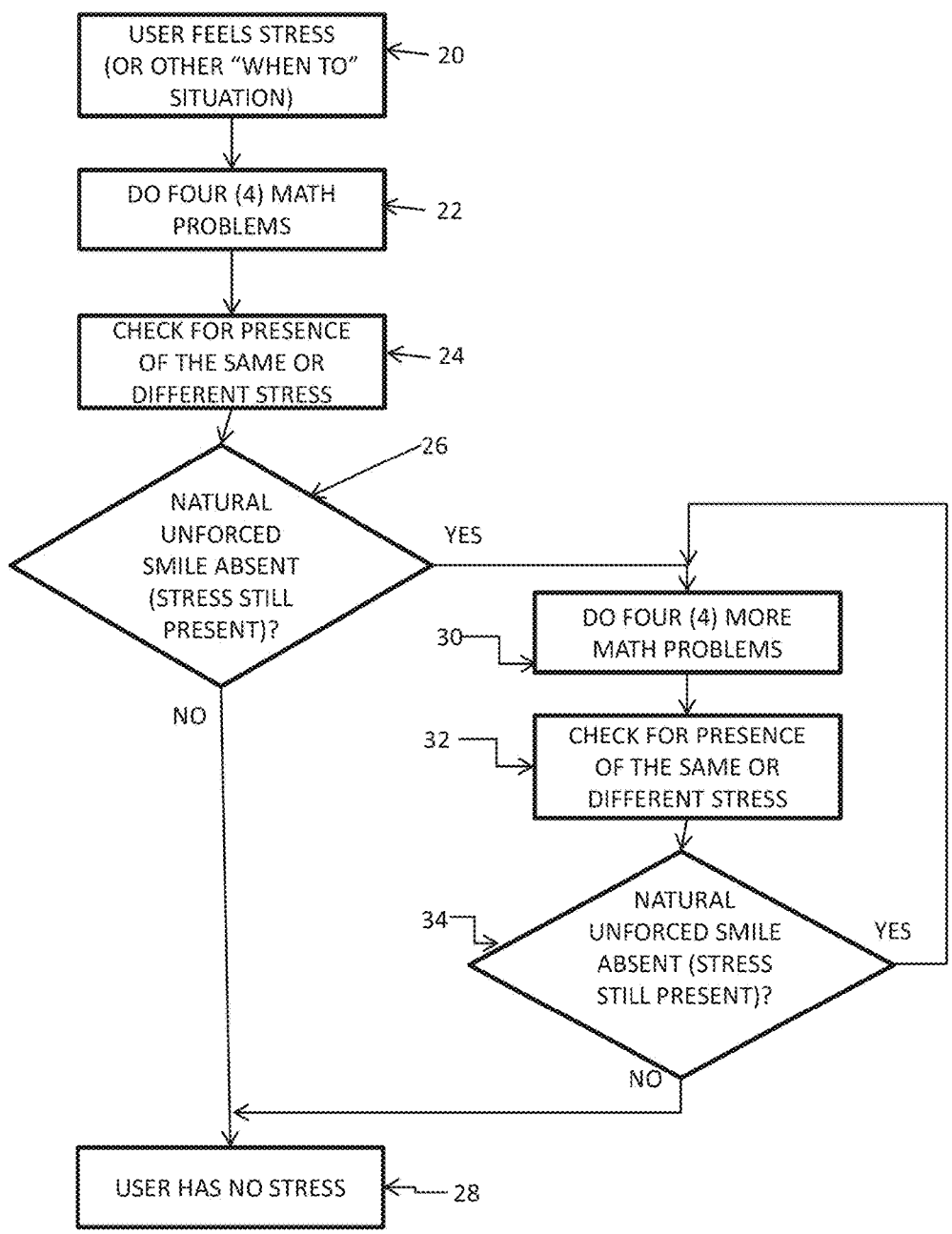
FIG. 3 is a drawing of flow chart of a method of one preferred embodiment.

As shown in FIG. 3, a method of Stress Conversion (from Uncontrollable Stress to Controllable Stress) in accordance with another embodiment of the invention is shown. A user first notes a list of "When To" situations found on one side of the Card at step 20. One such situation is when the user feels stress. The user may also use the Card when not under stress. (See description of FIG. 19, instructions section 55, herein, for examples of when to use the Card.)

At step 22, the user then does four (4) math problems from the Card or sheet. These are always done in one's head, and/or out loud. The number of repetitions of four (4) math problems sets, is done in whatever number as needed to get to a (Duchenne) smile. The problems are best done relatively quickly, within a few seconds (if it should take longer that is part of the procedure and is not prohibited), and must be single-digit arithmetic from the Card, which never employs division. Correctness of the answers is irrelevant.

At step 24, the user tries to re-experience the stress, anxiety or Stressor(s).

At step 26, the user determines subjectively whether any stress is still being experienced. If the stress has been converted (from Uncontrollable Stress to Controllable Stress—accompanied by a (Duchenne) smile), the user stops (step 28). If the stress is still present, the user does one or more cycles of four (4) math problems at step 30. The user then tries to re-experience the same stress again (or any other emergent stress) at step 32 (as in step 24). If any stress is still present, even if reduced (at step 34), the user (as desired) returns to step 30 and does more math problems. If/whenever the stress is now gone converted (from Uncontrollable Stress to Controllable Stress (accompanied by a Duchenne smile), the user ends the process at step 28.

If the user is using the Card at a period of non-stress, such as right after waking up or before going to sleep, on a regular basis such as three times a day, and/or before studying, reading, doing any activity requiring focus and heightened attention, then the process starts that way at step 20. Regardless of the reason for starting the process, the process is to be followed until the Duchenne smile is present.

III. Card Layouts, Formats, and Uses

Figure 4:
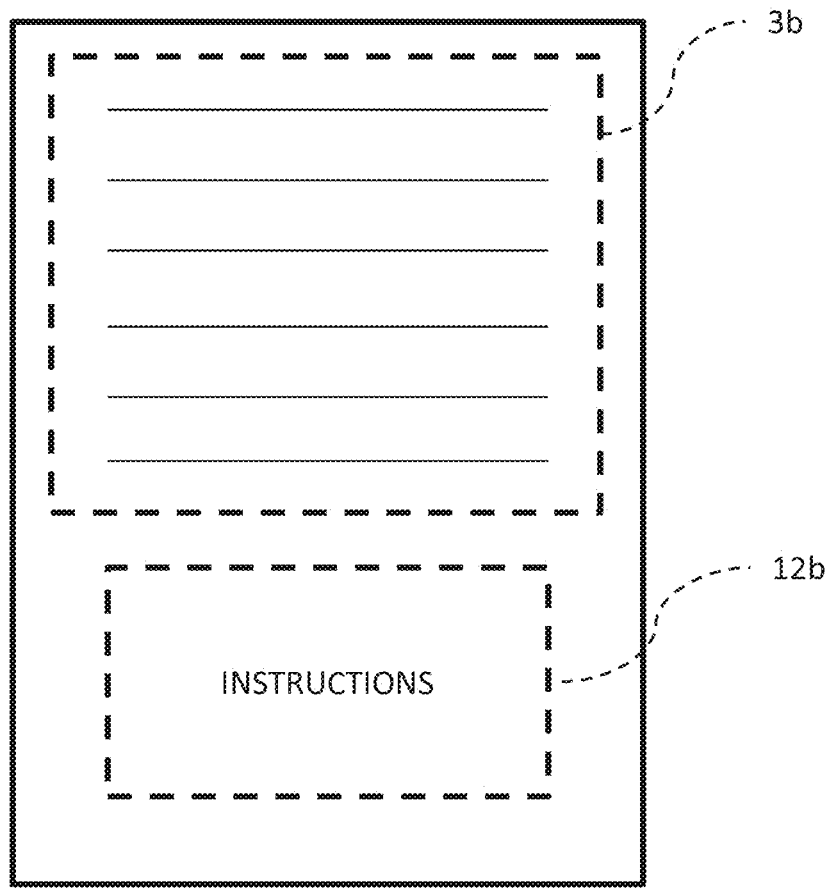
FIGS. 4, 5 and 6 are views of multiple Stress Conversion (from Uncontrollable Stress to Controllable Stress) Cards with various layouts.
Figure 5:
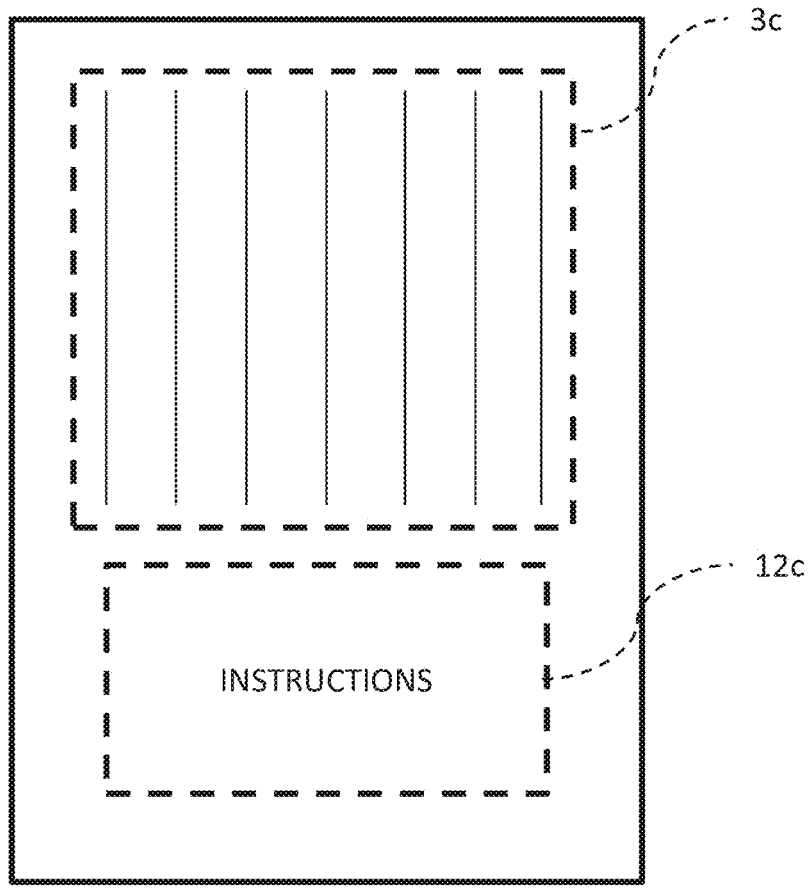
Figure 6:
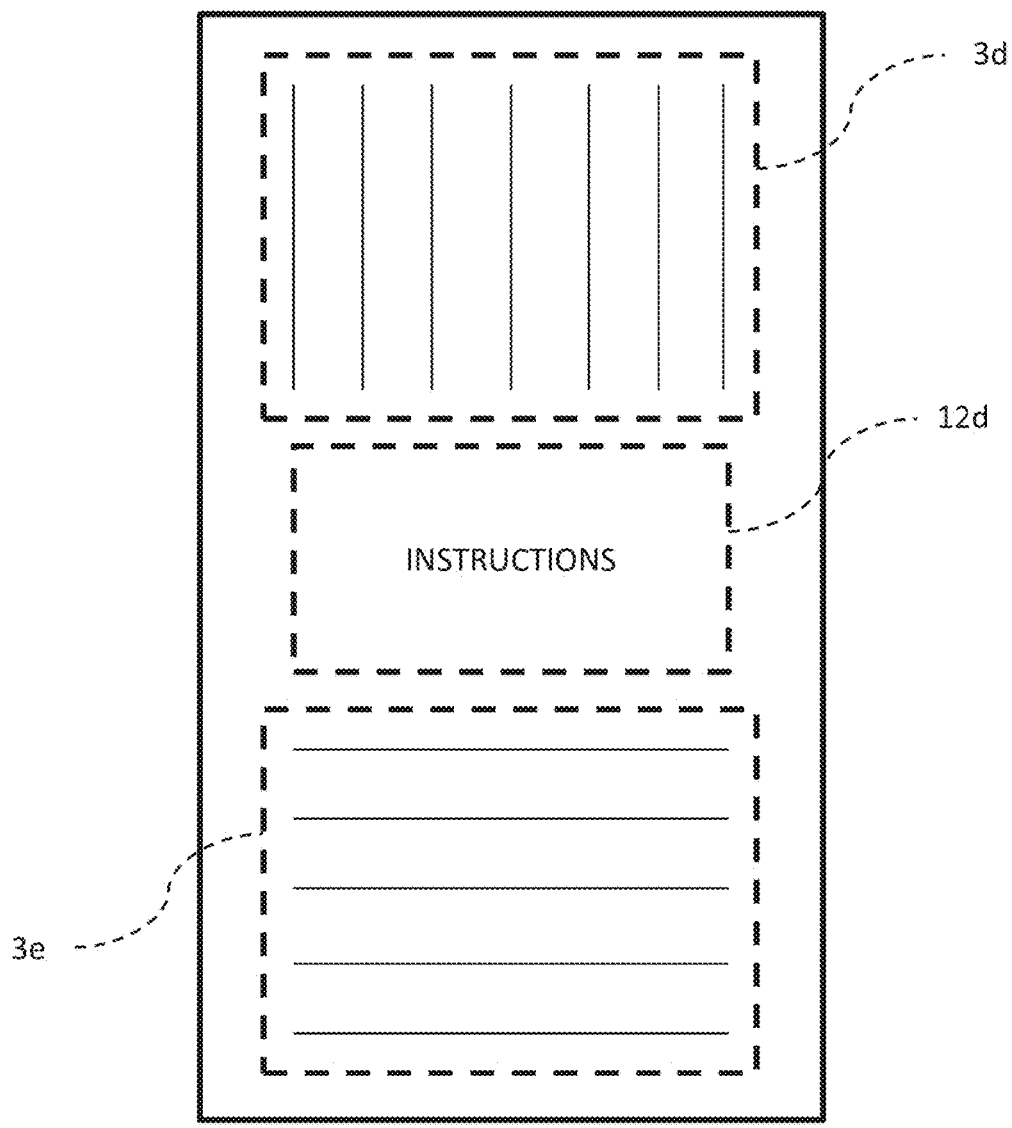

FIGS. 4, 5 and 6 are various Cards having alternative layouts of math problems and instructions. In FIG. 4, a Card has rows of math problems in math problem section 3*b*, and has instructions section 12*b*. In FIG. 5, a Card has columns of math problems in a math problem section 3*c* and has instructions 12*c*. In FIG. 6, there is a math problem section 3*d* with columns of math problems and a math problem section 3*e* with rows of math problems, and there are instructions 12*d*. The math problems of the Cards of FIGS. 4, 5, and 6 are problems of the same type (single digit addition, subtraction, and/or multiplication). The instructions are the same in substance as those of the other embodiments herein.

Figure 7:
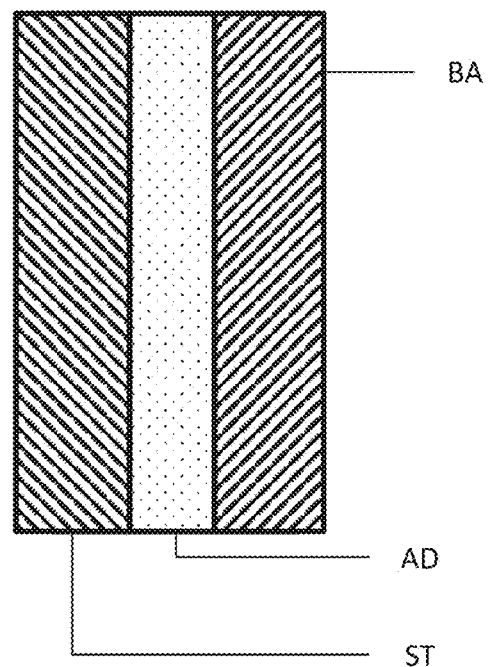
FIG. 7 shows an embodiment where the Card is formed as a sticker and FIG. 7A shows a placard.

In FIG. 7, the "Card" is shown as a sticker, e.g., a self-adhesive sticker having a plastic or plasticized layer ST which is opaque or clear, and an adhesive layer AD with a backing BA which is peel-able. The indicia, i.e., the math problems, may be provided on other media such as a non-bookmarked-shape card of any material. In this embodiment (and others), preferably two sets of math problems would be both on the same side of the card or sticker, or there may be a second card or sticker.

Figure 7A:
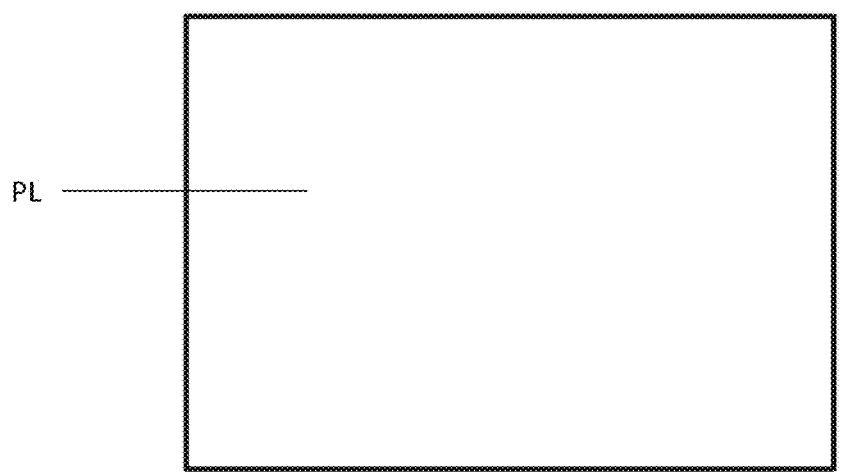

The Card PL is shown in FIG. 7A. It may be metal, wood, plastic or other relatively stiff material. The Card may be a card, sticker, paper, placard or whatever medium is used to display the math problems and instructions.

Figure 8:
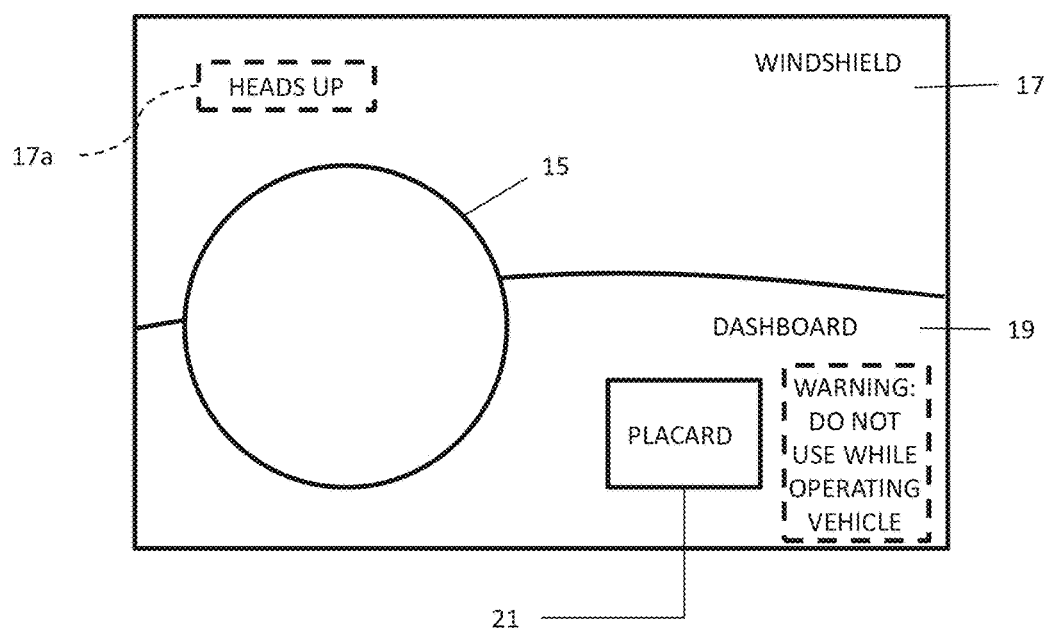
FIGS. 8, 8A, 9, 10, 11, 11A, 12, 12A, 12B, 13 and 14 are various embodiments where the Card is formed as a sticker, Card, or imprinting applied to various items.

In FIG. 8, the Card is shown as a sticker, imprint or placard 21 and is attached to the dashboard 19 of a vehicle, whether a bus, industrial vehicle such as a crane, a police vehicle, a fire truck, or other vehicle. The sticker (herein, sticker includes placard 21 or imprint, or other medium, unless unambiguously otherwise intended) may be placed on another part of a vehicle, where it may be seen by an operator or occupant. It may also or alternatively be embodied as a heads up display 17*a* on windshield 17. —In all cases involving a vehicle containing any version of an embodiment of the invention is to be accompanied by a warning to the driver/operator never to read from or use the Card while the vehicle is in motion and/or requiring the operator's full attention while driving/operating the vehicle.

Figure 8A:
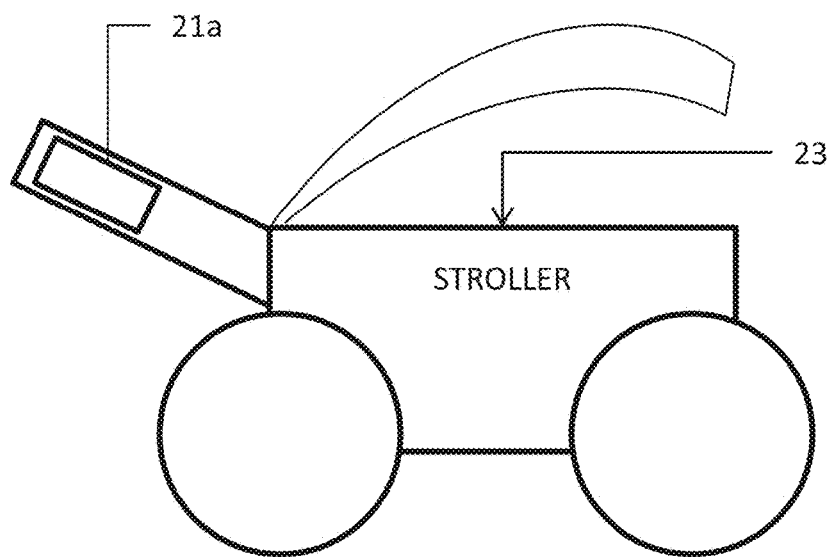

In FIG. 8A, a sticker 21*a* is placed on a baby stroller or carriage 23, or carrier, to help a parent or caretaker handle anywhere from occasional to repeated stress of caring for a baby or toddler.

Figure 9:
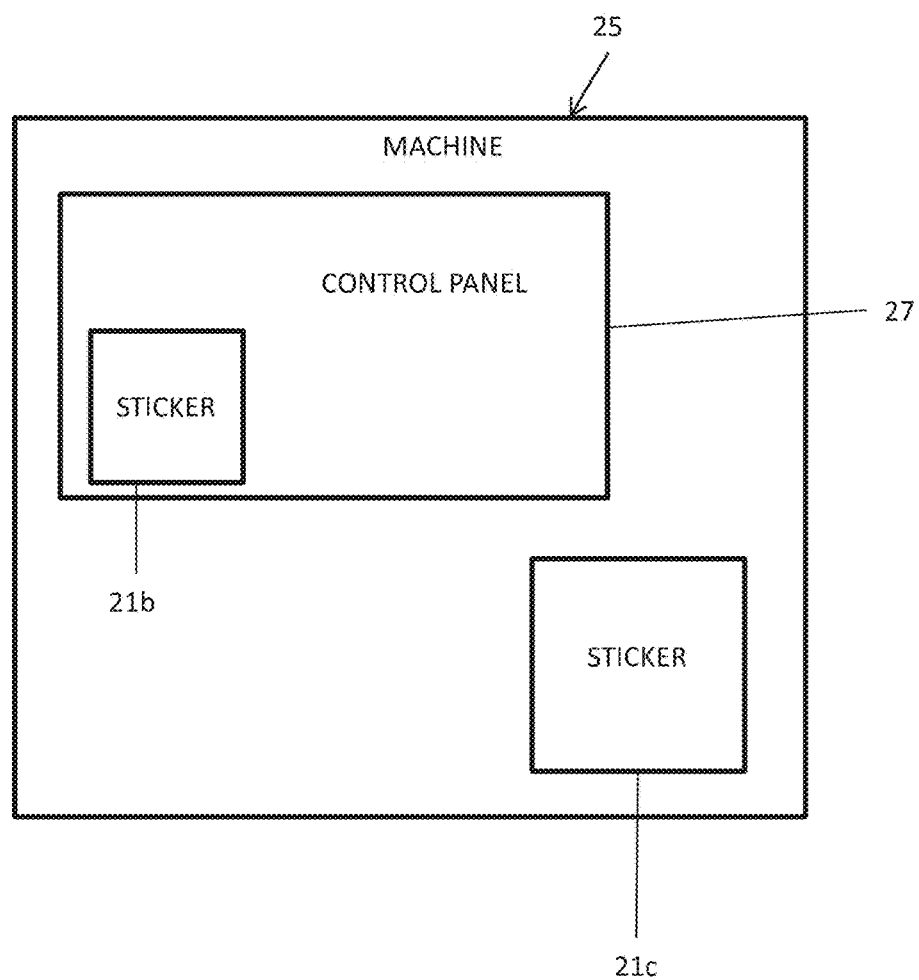

In FIG. 9, a sticker 21*b* (and/or sticker 21*c*) is placed on or adjacent a control panel 27 for a machine 25 of any sort, to help the operator handle stress. In all cases involving a vehicle containing any version of an embodiment of the invention, such embodiment is to be accompanied by a warning to the driver/operator never to read from or use the Card while the vehicle is in motion and/or requiring the operator's full attention while driving/operating the vehicle.

Figure 10:
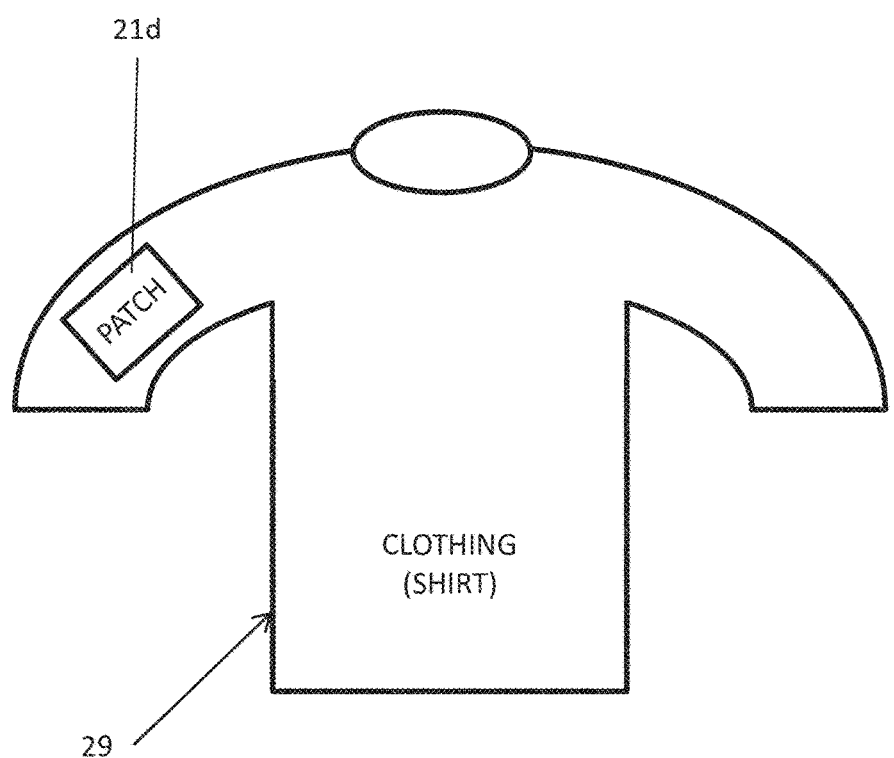

In FIG. 10, a sticker (which may also be a patch 21*d* or stitching in this instance) is on clothing 29, e.g., on a shirt sleeve. A police officer or firefighter or EMT worker or other high stress worker may find it helpful in this embodiment.

Figure 11:
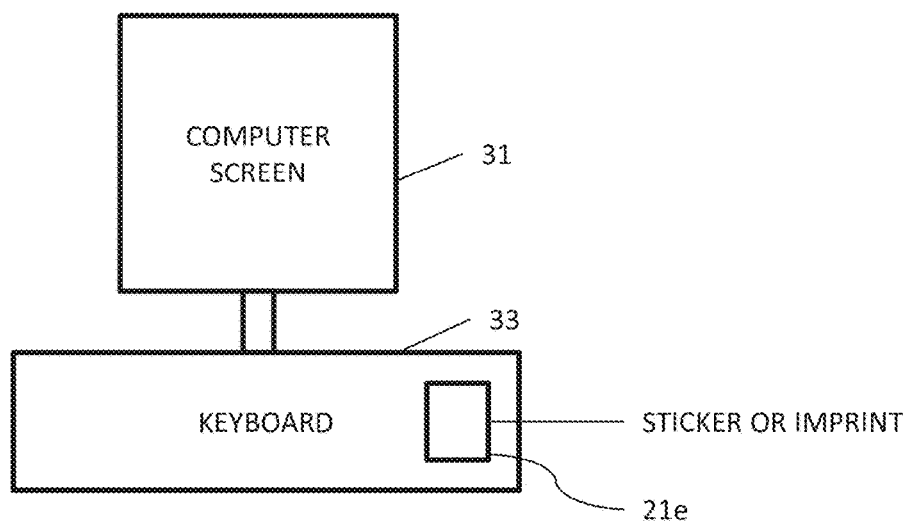
Figure 11A:
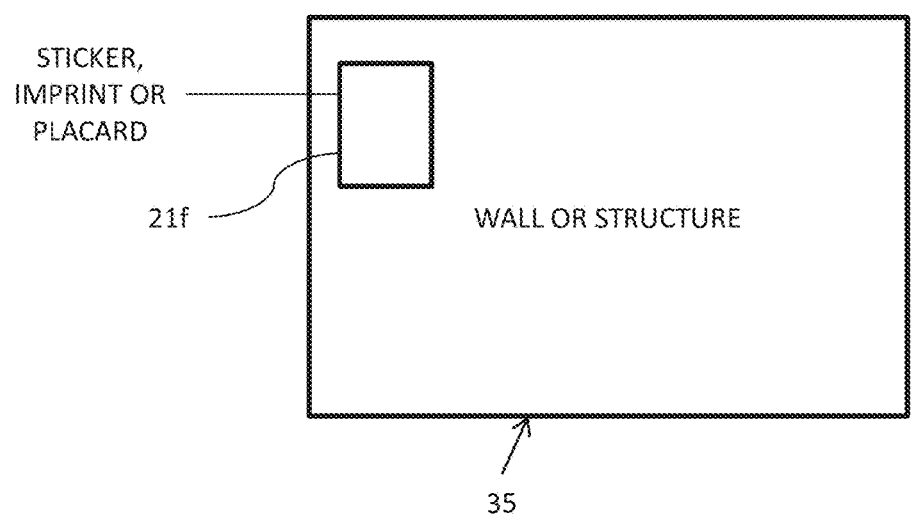

In FIG. 11, a sticker 21*e* is on a computer, e.g., on a keyboard 33 or fixed to a computer screen 31. In FIG. 11A, a sticker 21*f* is on a wall 35 or other portion of a structure. Such a wall or portion of the structure may be at or adjacent places where people wait in line, or commonly get stressed, such as at DMV, airport counters, airplane controllers' stations, train stations, subway stations, airplanes, and the like. In such places, the sticker could be on a sign on a stand too.

Figure 12:
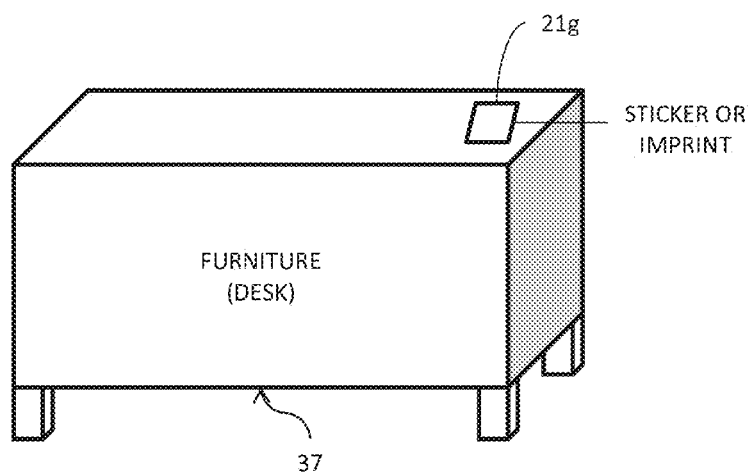
Figure 12A:
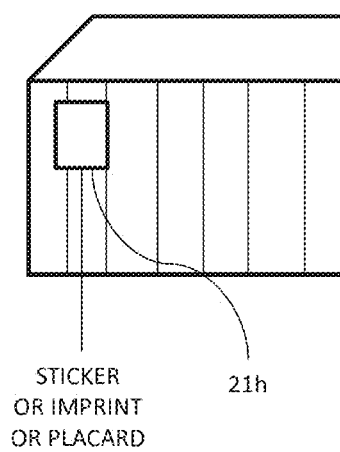
Figure 12B:
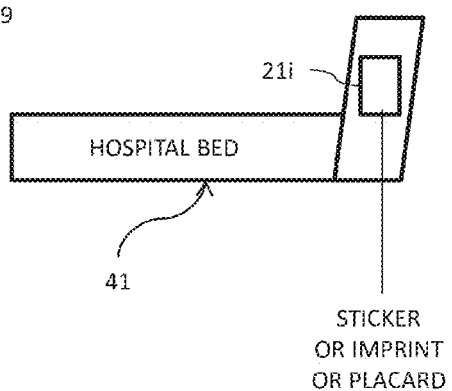

In FIG. 12, a sticker 21*g* is on furniture 37 or furnishings such as a desk. In FIG. 12A, a sticker 21*h* is on a crib 39 (or bassinet). In FIG. 12B, a sticker 21*i* is on a hospital bed 41 or other hospital location—In all cases involving healthcare related equipment containing any version of an embodiment of the invention, such embodiment (sticker and/or placard or the like) is to be accompanied by a warning to the operator never to read from or use the method while/whenever using the equipment, and/or that the equipment requires the operator's full attention.

Figure 13:
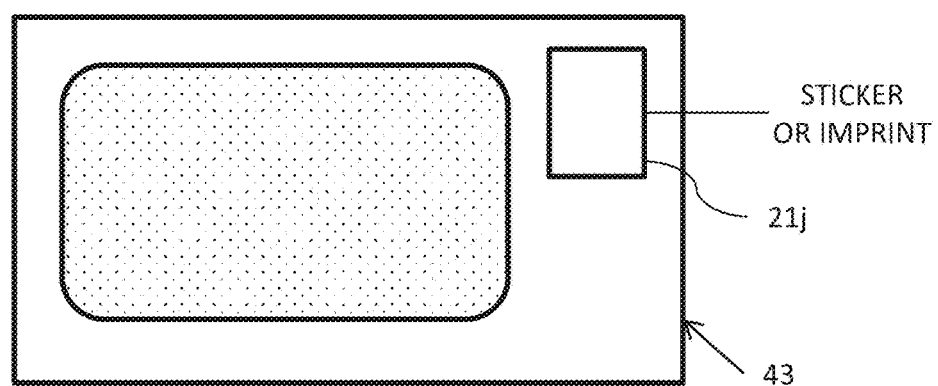
Figure 14:
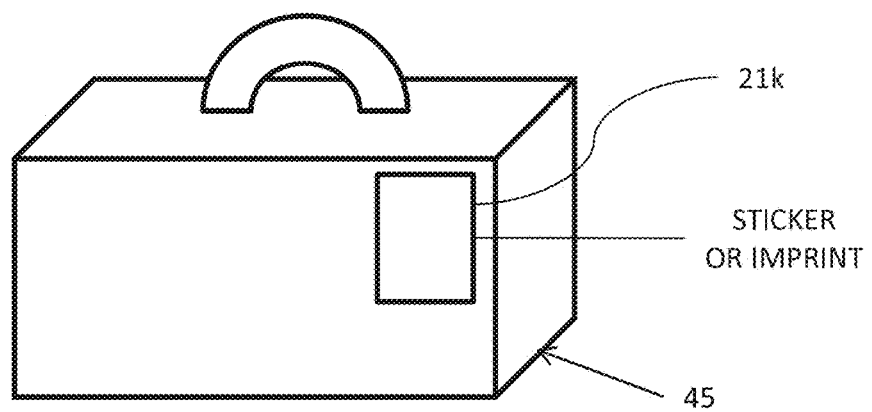

In FIG. 13, a sticker 21*j* is on an appliance 43 such as a microwave. In FIG. 14, a sticker 21*k* is on a briefcase 45, luggage or bag. Here, the sticker may also be a patch or stitched.

In the above embodiments, the sticker (or placard) may be clear, so that one can see the color of the item it is placed on.

Further embodiments include use of the Card on the following:

Card on heads up display of plane, jet, ship, train, bus, car, space shuttle or station, or other vehicle; —In all cases involving a vehicle/aircraft, etc., containing any version of an embodiment of the invention, such embodiment is to be accompanied by a warning to the driver/operator never to read from or use the Card while the vehicle/aircraft, etc., is in motion and/or requiring the operator's full attention while driving/operating the vehicle/aircraft, etc.

1. Card on baby carriage, crib, car seat, bottle
2. Card on hospital bed, tray, gurney, BP cuff, etc.
3. Card on stretcher, in ambulance (See above re warning to be used when operating moving vehicles), oxygen mask or tank, etc.
4. Card on ladder or bucket truck in bucket, or scaffolding, or window washing equipment, etc.
5. Card on air traffic controller controls
6. Card on heavy machinery (See above re warning to be used when operating precision, complex and/or heavy machinery)
7. Card in a machine (hand held) that displays various Cards, a cell phone, PDA, computer, etc.

8. Card in military, police, fire equipment (See above re warning to be used when operating moving vehicles).

Whether or not a warning sign is suggested herein, warnings should be placed as appropriate. In any event, the user should always use common sense as to the circumstances under which the Card is used.

IV. Additional Embodiments

The Stress Conversion (from Uncontrollable Stress to Controllable Stress) System and method of an embodiment of the invention may also be used to reduce anxiety and depression. For example, using the method and system daily or multiple times per day (according to the section, "When To Use" where it appears on different embodiments) will help reduce depression and/or anxiety, and raise the (No) Stress Threshold below which one is not upset by tumultuous events or toxic personalities. And this (No)Stress Threshold (below which one is not upset by tumultuous events or toxic personalities) has been reported by users to rise with continued Card use.

Figure 15:
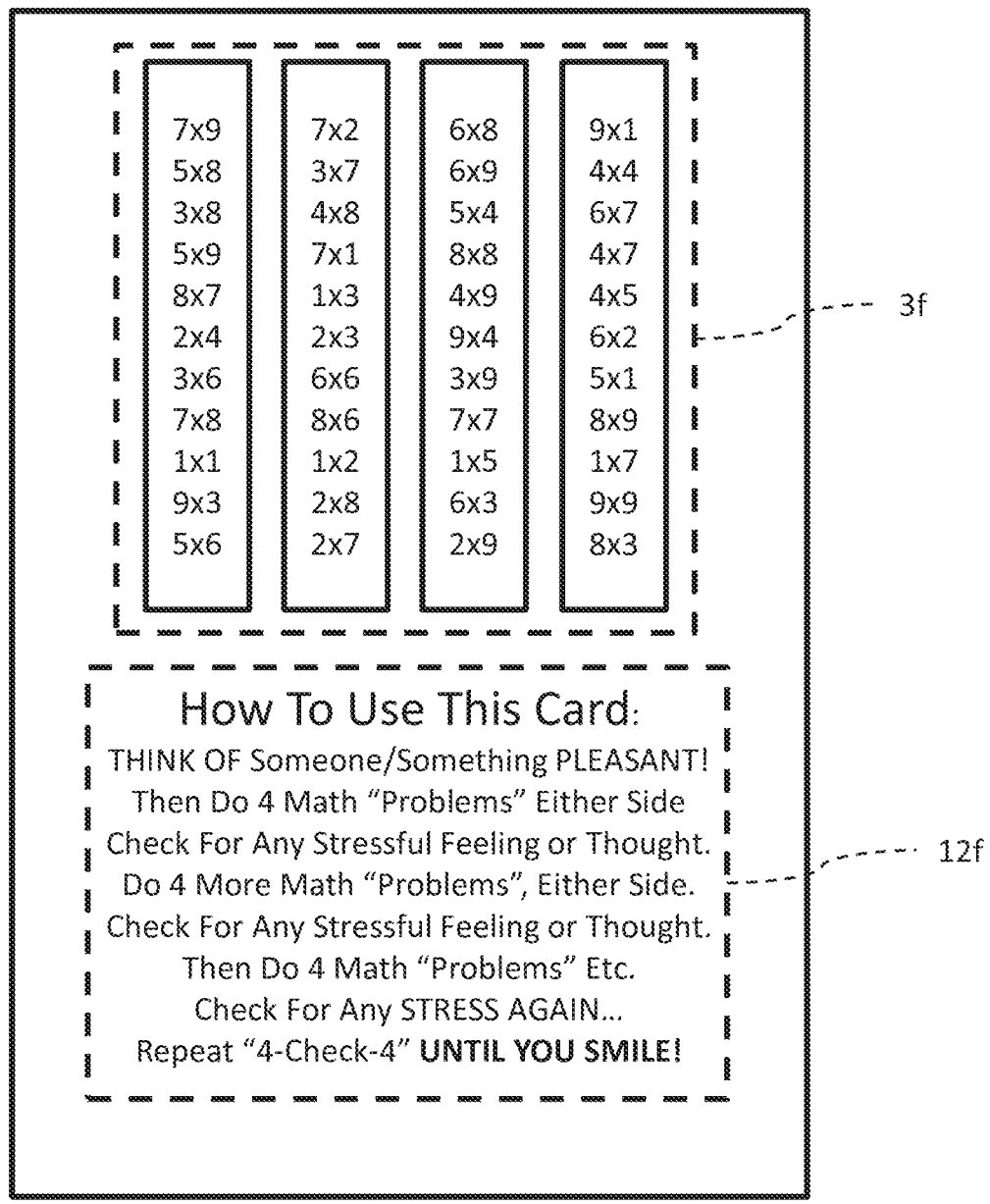
FIG. 15 shows another embodiment of the Card and method.

FIG. 15 shows a Card like that of FIG. 1, but of a different embodiment. In this embodiment, the Card contains rows and columns of math problems, e.g., having simple, single digit multiplication problems in a math problems section 3f. The Card may have an "educational" section on one edge or part, e.g., "THE OPPOSITE OF STRESS IS TRUST. Always Trusting Yourself and Inspiring Trust In Others . . . STARTS HERE!!!"

There is an instructions section 12f which may say what is shown in FIG. 15, or below, or the substantial equivalent thereof:

How To Use The TRUSTCard® . . .
Note: The Time (Of Day) The Stress (Extant) The Importance '(Of An Upcoming Decision)
 Then . . . Do 4 Math "Problems" Either Side.
 Check For Any Stressful Feeling or Thought.
 Do 4 More Math "Problems" Either Side.
 Check For Any Stressful Feeling or Thought.
 Do 4 More Math "Problems", Etc.
 Check For Any STRESS AGAIN . . .
 Repeat "4-Check-4" UNTIL YOU SMILE!

Pictures, phone numbers, copyright notice and other sayings may appear on the Card, All embodiments of the Card have single digit addition, subtraction, and/or multiplication problems. It may have an educational section as well, e.g., the same "saying" as in other figures herein. This Card may have instructions, Stress definition and Trust definition sections. On the back of the card, there may also be "instructions" which may say:

When to Use The TRUSTCard®
1 . . . 3× Every Day: At Times You Are Not Under Stress.
2 . . . Any Other Moment You Realize You Are Under Stress.
3 . . . When Possible Before Deciding Anything Important!
4 . . . 1st Thing After Waking; Last Thing Before Bedtime.
5 . . . At Moments of Recurring Fear, Worry, Upset or Dread!

The definition of "STRESS" and "TRUST" portions of this section preferably say:

STRESS DEFINED: WHEN YOU FEEL THE DEMANDS BEING MADE OF YOU EXCEED YOUR RESOURCES TO MEET THEM!

TRUST DEFINED: WHEN You (Would) FEEL 100% COMFORTABLE LETTING A PERSON (INCLUDING YOURSELF) MAKE DECISIONS OR ACT ON YOUR BEHALF There may also be other sayings, notices, copyright notice, such as or similar to on the Card of FIG. 15.

V. Physiological Changes

A. Brain Activation

For generation of ideas under stress, the inventor has combined and applied in a new way what is common knowledge in the field of neuroscience: that there are five Executive Functions of the Human Brain to be activated, and that each must be activated if an individual is to function at peak alertness, maximum reasoning capability and highest moral clarity. These five Executive Functions are selective attention, multiple factor awareness, decisions, voluntary movement, and resolution of conflicting information. The problem is that stress shuts down and/or hinders these functions, sometimes catastrophically while the brain is reeling under the onslaught of uncertainties and/or threats and/or dangers.

Users of the Card have reported that when they do not shrink from, but instead take note of (this does not mean ruminate about) uncertainty and then address the noted uncertainty using the Card; and do the same with any noted threat or danger in the course of normal life . . . the reduction of Uncontrollable Stress is accompanied by (as they report) an increasing trust in themselves to handle the demands around them.

Stress is biologically defined as whenever one feels the demands being made of one exceed one's resources to meet them, cognitively, emotionally or autonomically.

A recent study showed that a ratio score of Rumination[4] vs. Distraction was significantly associated with depressed and anxious symptoms over time. More specifically, individuals who have a greater tendency to Ruminate compared to Distracting themselves in precise and controlled ways, experience, for lack of the ability to distract themselves positively, increases in depression and anxiety scores over time, whereas those who have a greater tendency to engage in Distraction compared to Rumination have decreases in depression and anxiety symptoms over time.

[4] Rumination is defined as the compulsively focused attention on the symptoms of one's distress, and on its possible causes and consequences, as opposed to its solutions. Rumination is similar to worry except Rumination focuses on bad feelings, thoughts, images and experiences from the past, whereas worry is concerned with potential bad feelings, thoughts, images and experiences along with bad events in the future.

B. Physical Changes Corresponding to Stress and Stress Conversion (from Uncontrollable Stress to Controllable Stress)

Under stress, the ability to accurately remember and the ability to successfully predict are hampered. They are hampered because the circuits of the limbic system[5], specifically the left side amygdala[6] and its "allied brain structures and systems," take over and flood memory with past images of related (however distantly and irrelevantly to the present moment) uncertainties, threats, and/or dangers.

[5] The Limbic System is a ring of interconnected structures in the midline of the brain around the hypothalamus (see definition below).
[6] The Amygdala is a ganglion (any of certain masses of gray matter in the brain) of the limbic system adjoining the temporal lobe of the brain and involved in emotions of fear and aggression.

This leads to similar stress-based expectations about what will happen or what will be good or useful in the future based far too heavily on what happened in the past and significantly inconsequentially to what is also going on in the immediate present, which could dictate very different choices.

This is one of the most debilitating aspects of the stress response[7], which is reduced by using the systems and methods of various embodiments disclosed herein.[8]

[7] The Stress Response is when the Whole Brain/Whole Body Mobilization is to Run, Fight or Hide whenever Uncertain, Threatened and/or Endangered.
[8] The Thalamus is located in the middle of the brain and translates neural impulses from various receptors to the cerebral cortex, where they are experienced as the appropriate sensations of touch, pain, or temperature, during the waking state, and it regulates synaptic transmissions (i.e., incoming impulses) during resting states.

C. Operations and Physical Effects of Exemplary Embodiments

1. Experiencing Stress

In an example scenario, a user may experience a stressful event when seeing an oncoming car. Sensory input from the environment is recorded by specialized receptors embedded in sensory organs such as the eyes, ears and skin. The sensory input is converted through specialized "transformers" into nerve transmission. The nerve transmissions are then relayed to the sensory thalamus[8] (in the brain). The only exception is the sense of olfaction (smell) which is transformed into nerve impulses and relayed directly to the amygdala.

[8] The Thalamus is located in the middle of the brain and translates neural impulses from various receptors to the cerebral cortex, where they are experienced as the appropriate sensations of touch, pain, or temperature, during the waking state, and it regulates synaptic transmissions (i.e., incoming impulses) during resting states.

The thalamus has multiple functions. It may be thought of as switchboard of information. Although some initial sensory processing occurs in the thalamus, it is generally believed to act as a relay between a variety of sub-cortical[9] areas and the cerebral cortex.

[9] Sub-cortical . . . of or relating to or being or involving nerve centers below the cerebral cortex.

The sub-cortical area of significance in this summary is the amygdala, an almond shaped brain structure shown in research to perform a primary role in the processing of memory and emotional reactions. The cerebral cortex is the outermost layered structure of neural tissue of the brain and is divided into two hemispheres.

Figure 16:
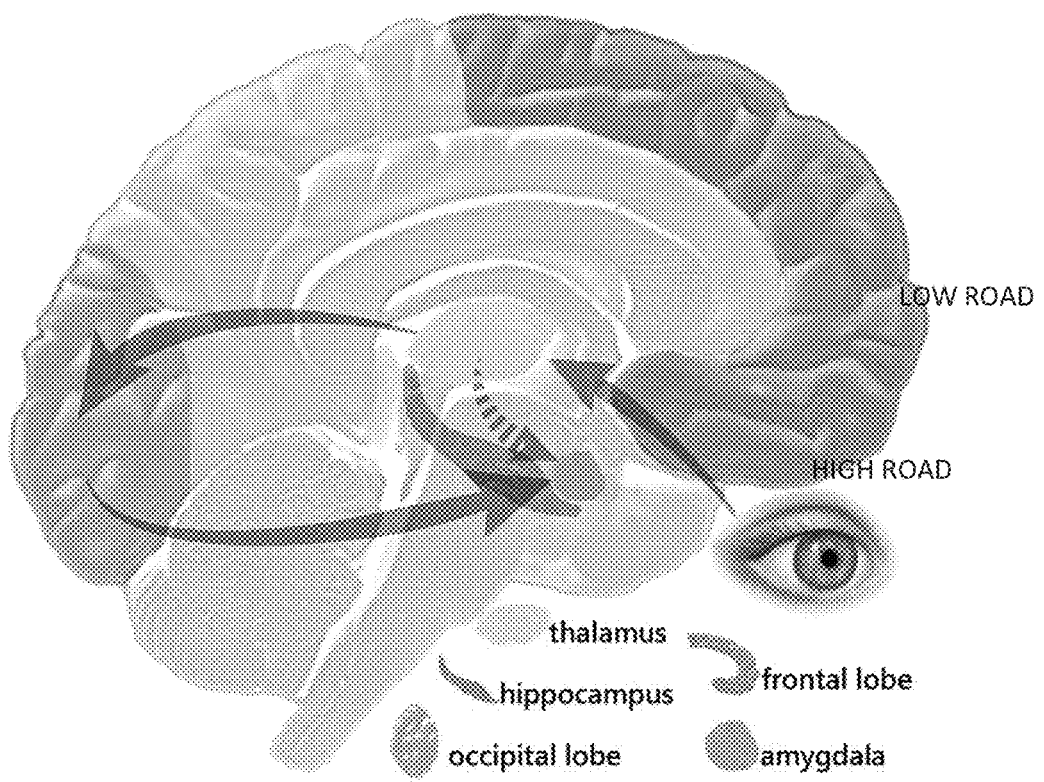
FIGS. 16-18 are schematic views to illustrate brain anatomy for explanatory purposes.

With reference to a schematic view of brain BR in FIG. 16, and using visual sensory input as an example, the sensory input enters the retina of eye EY and is sent via pathway SI to the lateral geniculate nucleus[10] of the thalamus TH, which in turn projects to the primary visual cortex in the occipital[11] lobe OL.

[10] The Lateral Geniculate Nucleus is formed by two bodies located inside the thalamus at the terminus of optic nerve fibers from the eyes. Geniculate means having kneelike joints or bends.
[11] Occipital means of or relating to the back of the head or skull.

In addition, and of utmost importance, are two other pathways which relay information to the amygdala AM. The so called "low road" broken arrow LR relays information directly from the sensory thalamus while another pathway, the "high road" arrows $HR_1$ and $HR_2$ relays information to the occipital cortex OC, i.e., the sensory cortex of the occipital lobe OL which then feeds back to the lateral amygdala[12] AM.

[12] The Lateral Amygdala is an Essential Locus of Fear Memory Storage.

The first pathway relays information from the sensory thalamus TH directly to the lateral nucleus (nucleus: a collection of nerve cell bodies) of the amygdala AM. To neuroscientist Joseph LeDoux, this initial relay from the sensory thalamus TH to the amygdala AM, the "low road," shown by arrow LR is a "quick and dirty" connection.

The "low road" is more primal in nature. Since it bypasses the sensory cortex, it only provides the amygdala AM with a crude representation of the external stimulus, for example the size, direction and/or speed of whatever is "out there." A big, fast thing coming at an individual, even if not consciously recognized, is probably best treated as a dangerous thing!

The lateral amygdala AM also gets inputs about a stimulus from another source. As already stated, it receives a crude but fast representation sensory input) from the sensory thalamus TH, but it also receives a slower but more complete representation from cortical sensory areas: in this example, from the visual cortex.

This latter cortical route includes several more synaptic connections than the sensory thalamus TH pathway to the lateral amygdala AM. Each synaptic link adds time to the transmission process, which is why cells in the lateral amygdala AM respond to information directly from the thalamus TH faster than they can respond to information from the cortex. More processing time by the brain means a slower mental and behavioral response from the organism. In situations in which rapid responses are required, speed can be more important than accuracy.

The so-called "high road" (pathway $HR_1$ and $HR_2$) provides feedback to the lateral amygdala AM from the cortex (at occipital lobe OL) as to what the origin of the uncertainty, threat or danger might have been influencing the amygdala by dampening the initial fear response or adding coals to the fire. The "low road" and the "high road" occur within milliseconds but the processing of the stimulus by the visual cortex and other cortical structures still have not delivered the stimulus to conscious awareness to the individual. The body and the brain can be in the early stages of a full throttled stress response and the owner of that body and brain is still not even consciously aware of the alarms firing off! (See FIG. 16)

Figure 17:
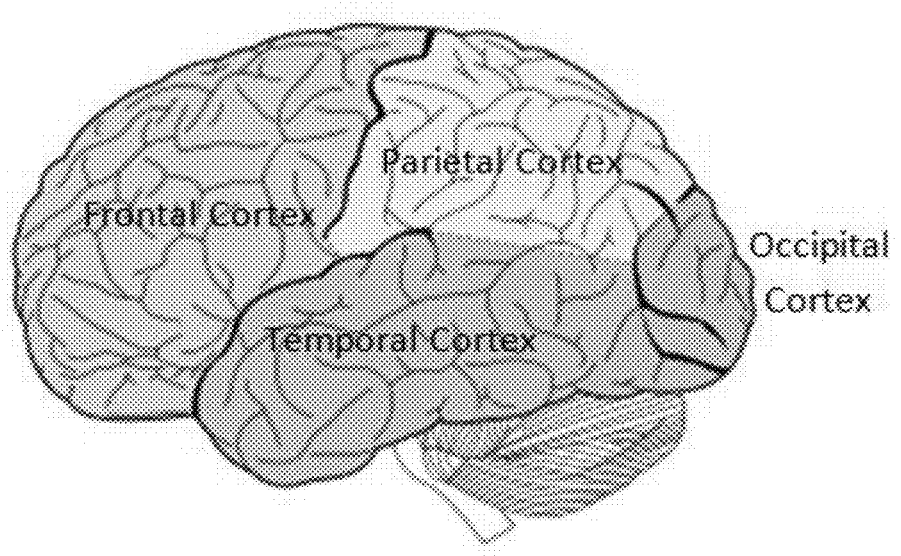
Figure 18:
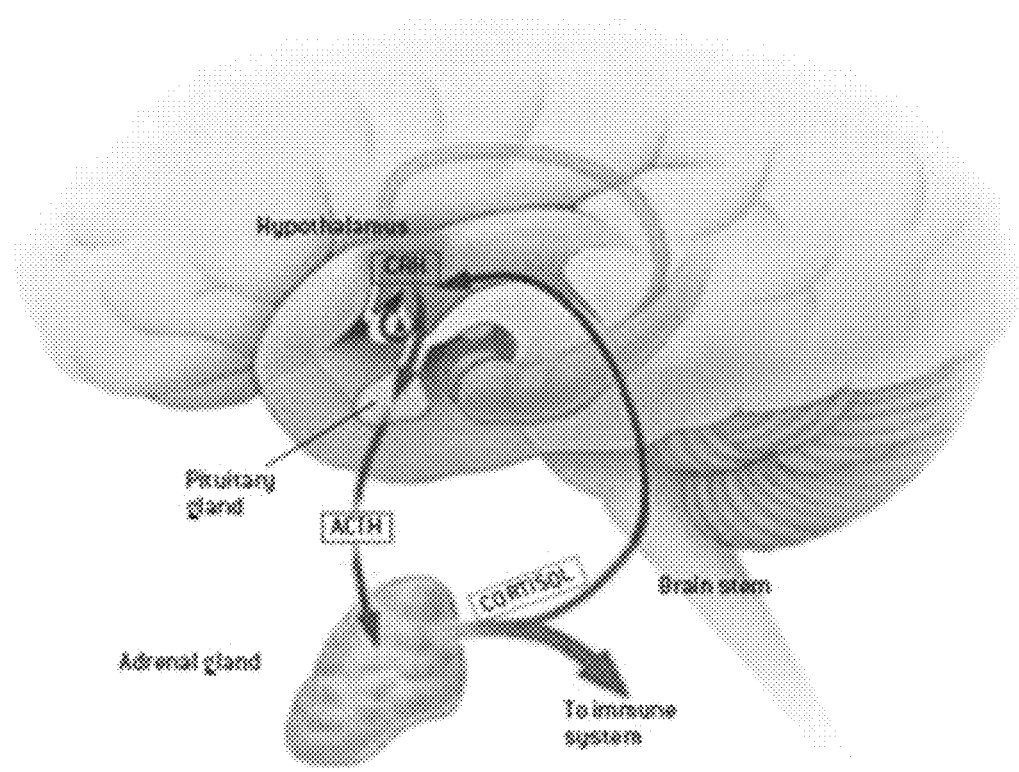

Sensory information arriving at the lateral aspect of the amygdala AM is processed and conveyed to the central nucleus of the amygdala, which is connected to ("projects") to several parts of the brain involved in responses to fear including conscious awareness of the stress producing stimulus. With continued reference to FIG. 16 and further schematic views of the brain shown in FIGS. 17 and 18, the brain areas involved in the ongoing fear response include the frontal cortex[13] FC, hippocampus[14] HI, hypothalamus[15] HY, the sympathetic nervous system[16], pituitary gland[17] PG and finally, glands resting on top of both kidneys, the adrenal glands[18] AG.

[13] Frontal Cortex is the portion of the cortex (covering) of the frontal lobe of the cerebral hemisphere. The frontal cortex is also called prefrontal area.
[14] Hippocampus is a convoluted, seahorse-shaped structure in the cerebral cortex of the temporal lobe of the brain. It forms part of the limbic system and is involved in the processing of emotions and memory.
[15] Hypothalamus is the part of the brain that lies below the thalamus, which controls the autonomic nervous system and the secretion of hormones by the pituitary gland. Through these nerve and hormone channels, the hypothalamus regulates many vital biological processes, including body temperature, blood pressure, thirst, hunger, and the sleep-wake cycle.
[16] The Sympathetic Nervous System is the part of the autonomic nervous system that tends to act in opposition to the parasympathetic nervous system, as by speeding up the heartbeat and causing contraction of the blood vessels. It regulates the function of the sweat glands and stimulates the secretion of glucose in the liver. The sympathetic nervous system is activated especially under conditions of stress.
[17] The Pituitary Gland is a gland at the base of the brain in vertebrate animals that is divided into two regions, anterior and posterior, each of which secretes important hormones. The anterior portion, whose secretions are directly controlled by the hypothalamus, produces hormones that regulate the function of most of the body's hormone-producing glands and organs, including the thyroid and adrenal glands. Growth hormone is also produced by the anterior pituitary.
[18] The Adrenal Glands trigger and modulate the body's overall response to stress (more below).

Each of the brain areas listed above will be discussed individually before they are tied together in coherent explanation of the next phase of the cascading stress response.

The frontal cortex FC is responsible for the qualities we think of as human. The frontal cortex FC allows the ability to recognize future consequences resulting from current actions, to choose between good and bad actions, override and suppress socially unacceptable responses, and determine similarities and differences between things or events. The frontal lobes FL also play an important part in retaining longer term memories which are not task-based. These memories are often associated with emotions derived from input from the amygdala AM and its other sub-cortical[19] allies. (See FIG. 17)

[19] Sub-Cortical is the matter of the brain situated beneath the cerebral cortex (the cortex being the furrowed outer layer of gray matter in the cerebrum of the brain, associated with the higher brain functions, as voluntary movement, coordination of sensory information, learning and memory, and the expression of individuality.)

Three aspects of the frontal cortex are particularly important to keep in mind in this summary. The first of the three functions is called "working memory". Working memory is the system that actively holds multiple pieces of transitory information in the mind, where they can be manipulated. Working memory includes subsystems in the frontal cortex FC that store and manipulate visual images or verbal information, as well as a central executive that coordinates the subsystems. It includes visual representation of the possible moves, and awareness of the flow of information into and out of memory, all stored for a limited amount of time. Working memory tasks require monitoring (i.e., manipulation of information or behaviors) as part of completing goal-directed actions in the setting of interfering processes and Distractions. The cognitive processes needed to achieve this include the executive and attention control of short-term memory, which permit interim integration, processing, disposal, and retrieval of information.

Working memory can be seen as using two different types of processing information. The two distinct processing types are called the phonological[20] Loop[21] and the visuo-spatial Sketchpad[22].

[20] Phonology is the study of the distribution and patterning of speech sounds in a language and of the tacit rules governing pronunciation.

[21] The Phonological Loop stores auditory information by silently rehearsing sounds or words in a continuous loop; the articulatory process (the "inner voice") continuously "speaks" the words to the phonological store (the "inner ear"). The phonological loop has a very limited capacity, which is demonstrated by the fact that it is easier to remember a list of short words (e.g., dog, wish, love) than a list of long words (e.g. association, systematic, confabulate) because short words fit better in the loop. However, if the test subject is given a task that ties up the articulatory process (saying "the, the, the" over and over again), then a list of short words is no easier to remember.

[22] The Visuo-Spatial Sketchpad stores visual and spatial information. It is engaged when performing spatial tasks (such as judging distance) or visual ones (such as counting the windows on a house or imagining images).

The phonological loop deals with sound or phonological information. It consists of two parts: a short-term phonological storage with auditory memory traces that are subject to rapid decay and an articulation rehearsal component that can revive the memory traces. Any auditory verbal information is assumed to enter automatically into the phonological storage. Visually presented language can be transformed into phonological code by silent articulation and thereby be encoded into the phonological storage.

The visuo-spatial sketchpad is assumed to hold information about what we see. It is used in the temporary storage and manipulation of spatial and visual information, such as remembering shapes and colors, or the location or speed of objects in space. It is also involved in tasks which involve planning of spatial movements, like planning one's way through a complex building. The visuo-spatial sketchpad can be divided into separate visual, spatial and possibly components of movements. It is principally represented within the right hemisphere of the brain.

The second function is called "Executive Functions." Executive Functions is an umbrella term for the management, regulation and control of cognitive processes including working memory, reasoning, task flexibility, problem solving, planning and execution. The executive system controls and manages other cognitive processes. It is responsible for processes that are sometimes referred to as Executive Functions, executive skills, supervisory attentional system, or cognitive control. The prefrontal areas of the frontal lobe are necessary but not sufficient for carrying out these functions as the entire brain is required The third function is "attention." Attention is the cognitive process of selectively concentrating on one aspect of the environment while ignoring other things. Attention has also been referred to as the allocation of processing resources. Attention is one of the most intensely studied topics in cognitive neuroscience in an attempt to the source of the signals that generate attention, the effects of these signals on the tuning properties of sensory neurons, and the relationship between attention and other cognitive processes like working memory and vigilance.

Five specific functions of working memory, attention and Executive Functions taken together which are important to consider in this summary are:
1. Selective Attention—what is focused on.
2. Mental Resource Allocation—which things in combination are considered.
3. Decision Making—choices between options, including goal prioritization.
4. Voluntary Movement—self-generated action.
5. Resolution Of Conflicting Stimuli—handling of situational contradictions.

The frontal cortex FC allows us to modify emotions under the right circumstances; this fact is a key to embodiments of the system and method as we will see later.

The hippocampus HI is a major component of the human brain and it plays important roles in the consolidation of information from short-term memory to long-term memory and spatial navigation. In the fear response the hippocampus HI provides context to the fear response. For example, based on short-term and long-term memory a snake behind a glass enclosure at the zoo will not trigger as great a fear response as a snake on the path in front of you on a hike in the mountains The sympathetic nervous system (SNS) is responsible for up-regulating and down-regulating homeostasis[23] in living organisms. Homeostasis refers to the body's ability through regulation by the nervous system and the endocrine system to maintain a stable, relatively constant condition. Fibers from the SNS innervate[24] tissues in almost every organ system, providing at least some regulatory function to things as diverse as pupil diameter, gut motility, and urinary output. It is perhaps best known for mediating[25] the neuronal and hormonal stress response commonly known as the fight-or-flight response.

[23] Homeostasis is the tendency of a system, especially the physiological system of higher animals, to maintain internal stability, owing to the coordinated response of its parts to any situation or stimulus that would tend to disturb its normal condition or function.

[24] To Innervate is to communicate nervous energy to; stimulate through nerves.

[25] To Mediate is to serve as a medium for causing (a result).

The other side of the autonomic nervous system is the parasympathetic nervous system which is responsible for "resting-and-digesting." The comprehensive functions of both the parasympathetic and sympathetic nervous systems are not so straightforward, but this is a useful rule of thumb.

The hypothalamus HY has many functions but the important function in this summary is that the hypothalamus HY links the current activity in the brain and nervous system to the endocrine system via the pituitary gland PG. This link, from the nervous system which activates within milliseconds but dissipates relatively quickly to the endocrine system which activates more slowly but can remain active for long periods of time is an essential consideration in the persistence of the stress response over time. The hormone[26] released by the hypothalamus HY with the target being the pituitary gland PG that links the nervous system to the endocrine system is Corticotropin-Releasing Hormone (CRH). We will later see that another hormone released by the hypothalamus, Oxytocin, is very important to the system and method.

[26] A Hormone is a chemical substance produced in an endocrine gland and transported in the blood to a certain tissue, on which it exerts a specific effect.

The endocrine system refers to the collection of cells, glands, and tissues of an organism that secrete hormones directly into the bloodstream to control the organisms' physiological and behavioral activities.

The pituitary gland PG is a protrusion off the bottom of the hypothalamus HY at the base of the brain. The pituitary gland PG secretes nine hormones that regulate homeostasis but the hormone important in this summary is Adrenocorticotropic hormone (ACTH).

The adrenal glands AG are endocrine glands that sit at the top of the kidneys. They are primarily responsible for releasing hormones in response to stress through the synthesis of corticosteroids[27] such as cortisol and catecholamines[28] such as epinephrine (adrenaline) and norepinephrine.

[27] Corticosteroids are . . . 1) steroids—any of a large group of fat-soluble organic compounds, as the sterols, bile acids, and sex hormones, most of which have specific physiological action. 2) cortico—a combining form representing cortex, in compound words: e.g., corticosteroid. 3) corticosteroid—any of a group of more than 40 organic compounds belonging to the steroid family and present in the cortex of the adrenal glands. Of these substances, about six are hormones, secreted into the bloodstream and carried to other tissues, where they elicit physiological responses. The hormones are categorized, according to their principal effects on the target organs, as glucocorticoids (a class of steroid hormones that bind to the glucocorticoid receptor (GR), which is present in almost every vertebrate animal cell). The name glucocorticoid (glucose+cortex+steroid) derives from its role in the regulation of the metabolism of glucose, its synthesis in the adrenal cortex, and its steroidal structure. GCs are part of the feedback mechanism in the immune system that turns immune activity (inflammation) down. They are therefore used in medicine to treat diseases caused by an overactive immune system, such as allergies, asthma, autoimmune diseases, and sepsis or mineralocorticoids (a class of steroid hormones characterized by their influence on salt and water balances.)

[28] Catecholamine is any of several compounds occurring naturally in the body that serve as hormones or as neurotransmitters in the sympathetic nervous system. The catecholamines include such compounds as epinephrine, or adrenaline, norepinephrine, and dopamine.

The HPA axis refers to the functional connections between the hypothalamus HY, pituitary gland PG and the adrenal gland AG.

Sensory information arriving at the lateral aspect of the amygdala AM is processed and conveyed to the central nucleus, which projects to several parts of the brain involved in responses to fear. At the hypothalamus HY, fear-signaling impulses activate both the sympathetic nervous system and the modulating systems of the HPA axis.

Stimulation of the adrenal gland AG by the sympathetic nervous system results in the secretion of the hormones . . . epinephrine also called adrenaline, nor-epinephrine[29] and a small amount of dopamine[30] into the blood stream. Because the sympathetic nervous system exerts direct control over the adrenal gland AG the release of epinephrine and norepinephrine can occur very quickly. This quick release of epinephrine into the blood stream can be considered the second phase of the acute stress response following the nervous system based initial phase described above.

[29] Nor-epinephrine is a neurotransmitter (chemical messenger in the brain), released by nerve terminals in the autonomic and possibly the central nervous system, that have such effects as constricting blood vessels, raising blood pressure, and dilating bronchi (the two channels into the lungs carrying air).
[30] Dopamine is a neurotransmitter (chemical messenger in the brain), in the central nervous system, retina, and sympathetic system, acting within the brain to help regulate movement and emotion: its depletion may cause Parkinson's disease.

The systemic effects of epinephrine include increased heart rate and blood pressure, blood vessel constriction in the skin and gastrointestinal tract, bronchiole[31] and capillary dilation, and increased metabolism, all of which are characteristic of the fight-or-flight response.

[31] Bronchiole is a small air sub-passage into the lungs.

In summary, the onset of a stress response is associated with specific physiological actions in the sympathetic nervous system, both directly and indirectly through the release of epinephrine from the adrenal glands AG. Epinephrine facilitates immediate physical reactions by triggering increases in heart rate and breathing and constricting blood vessels. The individual is now consciously aware of the acute stress he/she is feeling and now according to our research, something can be done about it.

In addition, the fear-signaling impulses generated by the amygdala AM have also activated the HPA (hypothalamus-pituitary-adrenal) axis through the release of corticotrophin releasing☐hormone[32] (CRH) from the hypothalamus HY. CRH from the hypothalamus HY stimulates the pituitary gland PG to release Adrenocorticotropic hormone (ACTH) which courses through the blood stream eventually stimulating the adrenal gland AG to secrete the hormone cortisol into the blood stream.

[32] Corticotropin Releasing Hormone (CRH) causes the anterior pituitary to release corticotropin which travels down to the adrenal cortex (the outer part of the adrenal gland), stimulating its growth and its secretion of corticosteroids (cortisone-like hormones). Cortisone is used in medicine to treat some forms of arthritis and to reduce inflammation. Cortisone is also a hormone that is produced by the anterior lobe of the pituitary gland and that stimulates the secretion of various hormones by the adrenal cortex.

A high level of cortisol in the blood stream is a marker[33] of chronic stress. Chronic stress is the response to, among other things, emotional pressure suffered for a prolonged period over which an individual perceives he or she has no control. While the immediate effects of stress hormones are initially beneficial in a given situation, long-term exposure to stress creates a high level of these hormones that remains constant. This typically leads to high blood pressure, heart disease, damage to muscle tissue, inhibition of growth, suppression of the immune system, and damage to (what has been over the last century, referred to as) mental health. (See FIG. 18)

[33] Marker (Biomarker) is a substance used as an indicator of a biologic state.

In an acute stress response the sympathetic branch of the nervous system is activated releasing epinephrine and nor-epinephrine as described above. Humans and other animals exposed to distressing events over which they have no control respond by releasing cortisol. If the stress hormones remain at high levels for prolonged periods of time it can lead to structural changes in the brain. Changes can occur to neurons and their synapses in the hippocampus HI and medial prefrontal cortex[34] PC. These changes produce impairments in working memory, spatial memory and produce increased aggression.

[34] Medial prefrontal cortex is a brain structure that participates in decision-making and emotion regulation.

In addition, the structural impairment of the medial prefrontal cortex results in deficits in the sub-cortical structures to which it is connected. This can bias decision-making strategies, as affected individuals shift from flexible behavior to one dominated by habit. Negative changes can also occur to dopamine activity in the prefrontal cortex PC.

The prefrontal cortex PC and the amygdala AM are reciprocally related. In order for the amygdala to respond to fear reactions, the prefrontal region has to be shut down. When the prefrontal region is active, the amygdala is inhibited making it harder to express fear. Pathologic fear, then, may occur when the amygdala AM is unchecked by the prefrontal cortex PC, and treatment of pathologic fear would have to assist a person to learn to increase activity in the prefrontal region so that the amygdala AM is less free and unfettered to express fear.

Decision-making ability is significantly impaired in humans when the prefrontal cortex PC is diminished and they are predisposed to develop fear and anxiety. Impaired Prefrontal function could be due to experiences that subtly alter prefrontal connections as described above. Fear reactions become difficult to regulate. Although objective information about the world may indicate that a situation is not dangerous, because a person cannot properly regulate fear circuits, they experience fear and anxiety in these (in fact, objectively) safe situations.

With the above understanding of the mechanisms of subconscious and conscious acute stress and chronic stress the value of the system and method in limiting the unavoidable moment to moment, and eventually recurring and/or ongoing stress becomes evident.

Other Definitions

A stressor is a chemical or biological agent, environmental condition, external stimulus or an event that causes stress to an organism. Events that trigger the stress response may include:

ENVIRONMENTAL STRESSORS (e.g., elevated sound levels, over-illumination, overcrowding)

DAILY STRESS EVENTS (e.g. traffic, lost keys, quality and quantity of physical activity);

LIFE CHANGES (e.g. divorce, bereavement);

WORKPLACE STRESSORS (e.g. high job demand v. low job control, repeated or sustained exertions, forceful exertions, extreme postures);

CHEMICAL STRESSORS (e.g. tobacco, alcohol, drugs); and

SOCIAL STRESSORS (e.g., societal and family demands).

Stressors create physical, chemical and mental responses inside the brain and body based on stimulation of the sympathetic nervous system and HPA axis described above.

Internal-Brain/Stressor-Impact Control

A tremendous amount of data has been accumulated that clearly demonstrates that an "Uncontrolled Stressor," with respect to which the individual lacks Internal-Brain/Stressor-Impact Control, has a negative impact on the individual not only at the time of the original "Uncontrolled Stress" but also has a lasting effect when the individual is under the influence of future Stressors. As little as one experience with an Uncontrolled Stressor predisposes the individual to react to future Stressors with difficulty, literally, with helplessness. Studies have also clearly indicated that Internal-Brain/Stressor-Impact Control implemented at the time of the original "Uncontrolled Stressor" can not only reduce the negative effect of the original Stressor but can have long lasting effects, a virtual "immunization" to future Stressors. The system and method are an Internal-Brain/Stressor-Impact Control Protocol for any individual using it during a stressful episode. Many individuals have reported this effect with respect to use during stress, and with respect to conversion (from Uncontrollable Stress to Controllable Stress), of subsequent stress or to effect avoidance of subsequent stress feelings. This is a very important point.

Neuroplasticity[35]/Synaptic[36] Plasticity

[35] Neuroplasticity is the brain's natural ability to form new connections in order to compensate for injury or changes in one's environment.

[36] Synapse is the small junction across which a nerve impulse passes from one nerve cell to another nerve cell, a muscle cell, or a gland cell.

Plasticity is an English word which means the capability of being molded, receiving shape, or being made to assume a desired form. Neuroplasticity refers to changes in neural pathways and synapses which are due to changes in behavior, environment and neural processes, as well as changes resulting from brain or body injury. Neuroplasticity has replaced the formerly-held position that the brain is a physiologically static organ. It has now been clearly proven that the brain changes throughout life.

In the brain, a synapse is a structure that permits one neuron (or nerve cell) to pass a chemical signal to another neuron. The chemical signalers are called neurotransmitters which pass through the small space between connecting synapses. Any one of the 100 (Adult)-200 billion (Late Adolescent) neurons in the brain can have up to 10,000 synapses each! In common language you may have heard the names of these neurotransmitters, names such as dopamine, serotonin[37] and adrenaline (also called epinephrine).

[37] Serotonin is a neurotransmitter that is formed from tryptophan, (a component of proteins necessary for growth) and found in many animal tissues, including the intestine and central nervous system. In the brain, serotonin acts as a neurotransmitter that is involved in the control of pain perception, the sleep-wake cycle, and mood. Serotonin is also produced in some bacteria and plants.

Synaptic plasticity is also well described as the ability of synaptic connections to strengthen or weaken over time, in response to increases or decreases in their activity. Plastic change also results from the alteration of the number of receptors located on a synapse. There are several underlying mechanisms that cooperate to achieve synaptic plasticity, including changes in the quantity of neurotransmitters (chemical messengers) released into a synapse and changes in how effectively cells respond to those neurotransmitters. Synaptic plasticity in both excitatory and inhibitory synapses exist. Excitatory (those which stir brain and body to some kind of action) and inhibitory (those which stop or prevent brain and body from starting or continuing some kind of action) synapses has been found to be dependent upon postsynaptic[38] calcium release. Since memories are represented by vastly interconnected networks of synapses in the brain, synaptic plasticity is one of the important neurochemical foundations of learning and memory. All learning, memory and behavior, all things human, are made possible by constant updating of synapse connections in your brain.

[38] Postsynaptic is the state of being or occurring on the receiving end of a discharge (of neurotransmitter/chemical messengers) across the synapse.

Neuroplasticity occurs on a variety of levels, ranging from cellular changes due to learning, to large-scale changes involved in cortical remapping in response to injury. It has now been proven that the brain remains plastic even into adulthood.

Decades of research have now shown that substantial changes occur in the lowest neocortical[39] processing areas, and that these changes can profoundly alter the pattern of neuronal (of brain cell) activation in response to experience. Experience can and actually does change both the brain's physical structure and functional organization.

[39] Neocortical area is the largest and evolutionarily most recent portion of the cerebral cortex, composed of complex, layered tissue, the site of most of the higher brain functions.

2. User Looks For Card

In consideration of all of the following data it is important to keep in mind that the system and method involve single-digit multiplication, addition and subtraction math equations (without answers), including proprietary directions for use, printed on a 6×2 inch laminated Card; similar in size and form to a bookmark. Studies have proven that the positive effects of solving single-digit math equations are limited to those involving addition, multiplication, and subtraction but do not extend to division equations!

During the stress response, the attention of working memory (described above) is forced onto the stressor at the expense of an individual's Internal-Brain/Stressor-Impact Control. In a pure, unstressed state, (which for most of us is not the norm[40] by any means much of the time despite our lack of awareness of the fact), an individual controls his/her focus, his/her multiple factor awareness, his/her decisions, his/her voluntary actions and has the ability to correct both incoming and outgoing contradictions, with respect to information and/or his or her own behavior. Considering the inverse relationship between the sub-cortical structures (amygdala) and the frontal cortex (specifically, the prefrontal cortex area), the user simply searching for the Card activates prefrontal circuits and tips the balance towards Internal-Brain/Stressor-Impact Control through decision-making. Due to the nature of physical Card embodiments of the system and method, Internal-Brain/Stressor-Impact Control through increased Executive Functions is started even before the system and method is fully engaged.

[40] Note: A 100% pure, unstressed state can be so rare for an individual that he or she considers themselves "in the zone" (a term of art used mostly in sports), whenever it might occur. Another way to say this is that it would be the state of mind accompanying a particularly good day which not much goes wrong and little resistances met with one's actions, goals and purposes or if present, whatever resistance seems to move itself away many the individual comes anywhere near it—an unusual state for any person. This note suggests and actually states outright that the condition of human being is more than not one of at least partial stress in the modern world and might be best understood as the precise state of mind or being we seek to escape from "on weekends", "on vacation", "at the movies" . . . .

Activation of prefrontal circuits occurs when for example, one is remembering the location of an object; the activation leaves two memory traces, one referring to its original location (an episodic record) and another referring to the new location (a working-memory trace). Thus, even before you actually delve all the way into the main body of the system and method, it will already have started to decrease stressful thoughts and feelings.

During stress, working memory is impaired. Even before using the system and method, simply thinking about where you left your Card activates the medial prefrontal cortex and as stated above, when prefrontal circuits are activated the amygdala is inhibited, making it harder for the amygdala to express fear.

3. User Grasps a Card

Grasping a Card activates the parietal lobe[41]. The parietal lobe plays important roles in integrating sensory information from various parts of the body, knowledge of numbers and their relations, and in the manipulation of objects. Its function also includes processing information relating to the sense of touch. Portions of the parietal lobe are involved with visuo-spatial processing. Grasping a Card redistributes blood flow in the brain due to the extensive activation of neurons in the parietal lobe.

[41] The Parietal Lobe plays important roles in integrating sensory information from various parts of the body, knowledge of numbers and their relations, and in the manipulation of objects. Portions of the parietal lobe are involved with visuospatial processing. Although multisensory in nature, the posterior parietal cortex is often referred to by vision scientists as the dorsal stream of vision (as opposed to the ventral stream in the temporal lobe). This dorsal stream has been called both the 'where' stream (as in spatial vision) and the 'how' stream (as in vision for action). Various studies in the 1990s found that different regions of the posterior parietal cortex in Macaques represent different parts of space.

The function of an object such as drinking coffee is bound in our memory to the object itself such as a coffee cup. This object-function binding also occurs with the system and method. Once a person has used embodiments of the system and method, the actions performed in finding it, grasping it and using it for the purpose of Internal-Brain/Stressor-Impact Control in personal stress intervention forms a lasting representation in the brain.

4. User Places Card within his/her View

The Object-Action binding (see above) is a critical component of the positive results produced by seeing a Card. Studies of the "Priming Effect" an implicit (subconscious) effect in which exposure to a stimulus influences a response to a later stimulus. Once a Card is bound to personal stress intervention it has a positive priming effect on an individual's response to a later Stressor. In this way, the Card becomes a positive, self-generated environmental cue which commences Internal-Brain/Stressor-Impact Control.

5. User Picks a Side to Use and Orients to the Card

A portion of the parietal cortex PC, the lateral intraparietal area, contains a map of neurons, encoded when the eyes are fixed on a particular location, representing the saliency[42] of spatial locations, and attention to these spatial locations. Changing the direction of eye movement during a stressful episode decreases the vividness of the stressful memory.

[42] Saliency is the state or condition or being prominent, conspicuous or striking.

In addition, simultaneous activation of the visuo-spatial sketch pad, looking at an object, holding an object, and moving an object activates the visuo-spatial sketch pad. Together with activation of the phonological loop (see below) dual activation of the visuo-spatial sketchpad and phonological loop more effectively decreases intensity of negative emotions than activation of either system alone further demonstrating the importance of the physical Card.

6. User Chooses a Math Problem

Even before engaging in "doing the math" an individual choosing a particular side of the Card, addition and subtraction or multiplication, is exercising Internal-Brain/Stressor-Impact Control over a Stressor. Internal-Brain/Stressor-Impact Control imparts the benefits of "immunization" to later Stressors as discussed above. Studies indicate that the positive benefits of Internal-Brain/Stressor-Impact Control over a prior Stressor are of utmost importance.

7. User Reads a Math Problem

The phonological loop (see above) is that portion of working memory which holds sound or phonological information for processing. Auditory or verbal information is assumed to enter automatically into the phonological storage. Visually presented language can be transformed into phonological code by silent articulation and thereby be encoded into the phonological storage (or store). Simultaneous activation of the phonological loop along with activation of the Visuo-spatial sketch pad more effectively decreases intensity of negative emotions than activation of either system alone.

For example: Converting the visual equations on the Card to phonological information, manipulating the equations, articulating the answers either out loud or silently activates these two systems more efficiently and effectively than either processing function alone. This further demonstrates the unique importance of placing single-digit math equations on the physical Card.

Directed eye movements during the recall of negative emotion images (remembering) by an individual potently decrease both the vividness and intensity of the recalled memory. Specifically, the eye movements required to see an individual math equation such as addition, subtraction and multiplication decrease intensity and vividness of negative emotional memory. This again is consistent with the use of single digit math equations on the physical Card.

8. User States or Considers the Math Problem

Reiterating . . . the phonological loop is that portion of working memory which holds sound or phonological information for processing. Auditory or verbal information is assumed to enter automatically into the phonological store. Visually presented language can be transformed into phonological code by silent articulation and thereby be encoded into the phonological storage.

More brain activation can occur when the equations are answered out loud; that said, the same areas in the brain and the same nerves which innervate the muscles of facial expression and articulation are activated to one degree or another whether the answers are articulated out loud or silently.

9. User Formulates an Answer to the Math Problem

The regulation, control, manipulation and management of cognitive processes such as planning, working memory, attention, problem solving, verbal reasoning, inhibition, mental flexibility, task switching and initiation and monitoring of actions has been labeled "Executive Functions." The more Executive Functions are engaged the less the "stress circuits" of the brain are engaged. Single digit multiplication engages Executive Functions related to memory diverting limited working memory resources away from the stress circuits.

As stated just above, the more Executive Functions are engaged the less the "stress circuits" of the brain are engaged. Single digit addition and subtraction engage executive functions related to actual computation (we calculate 5+8=13) while single digit multiplication engage executive functions related to memory (we remember 2×4=8). A single digit math equation is indeed a very powerful thing, activating memory and decision-making Executive Functions in an emotionally neutral manner diverting even more of the limited working memory resources away from the stress circuits.

The system and method relies on numerical Distraction as a method proven to disrupt negative emotions and improve negative mood. Numerical Distraction, the use of single digit addition, subtraction and multiplication, used at the same time that stress and intrusive negative thoughts corrupt our ability to think clearly and enjoy life, improves negative mood, decreases the body's physiologic stress response (increased heart rate, sweaty palms, rapid breathing etc.) and interrupts negative thoughts. Numerical Distraction works faster and more completely than other forms of Distraction.

Single digit math is an emotionally neutral stimulus. The nature of the task used to compete with the forced attention on negative thoughts is of utmost importance. Emotionally neutral tasks like single digit math equations are much more effective than similar tasks with positive or negative emotional weight.

Working memory load is self-balanced vs. any Stressor to equilibrate[43] working memory load.

[43] Equilibrate . . . to balance equally; keep in equipoise or equilibrium.

As stated before, working memory is generally considered to have limited capacity. Working memory load also called cognitive load refers to the amount of data being manipulated by working memory at any particular time. As previously stated, alternating between two tasks alters each of the tasks to one degree or another. It has also been clearly demonstrated that in order to reduce stressful feelings the "other" task load must be balanced with the demands on working memory of the stressful thoughts or feelings. The system and method's use of single digit math is an excellent solution. The individual can alter the type of equation, the difficulty, the pace, the length of time and many other factors which balance the cognitive load with the demand of the stress producing thoughts.

10. User States the Answer Out Loud

As stated above (and in section/step 8 above), the phonological loop is that portion of working memory which holds sound or phonological information for processing. Auditory or verbal information is assumed to enter automatically into the phonological storage. Visually presented language can be transformed into phonological code by silent articulation and thereby be encoded into the phonological storage.

In addition, more brain activation can occur when the equations are answered out loud; however, the same areas in the brain and the same nerves which innervate the muscles of facial expression and articulation are activated to one degree or another whether the answers are articulated out loud or silently.

11. User Repeats Steps 5-10 Three More Times

Due to synaptic plasticity and neurogenesis (the formation of new neurons) the changes are physical and cumulative. Neuroscientists described the effect of repeated use of the system and method use in the following phrase:

NEURONS THAT FIRE TOGETHER WIRE TOGETHER.

There are complex progressive changes that physically occur in synapses, neurons, neurotransmitters, glial cells (a class of brain cells once thought to be limited to supporting roles but now believed to be involved in wholesale brain "rewiring"), receptors, cell membranes and others.

12. User Checks for Stress and Repeats Steps 5-12 as Needed to Reach 13

The user checks for any residual stress. The user continues the 4×4 check until he/she (Duchenne) smiles naturally.

The method of alternating tasks as in embodiments of the system and method eliminates "thought suppression" a proven-to-be ineffective method for dealing with stress. Thought suppression is a mental process of deliberately trying to stop thinking about certain thoughts. It is often associated with obsessive-compulsive disorder in which a sufferer will repeatedly (usually unsuccessfully) attempt to prevent or "neutralize" intrusive distressing thoughts. This technique, although still used today, has been proven to not only be ineffective in "neutralizing" distressing thoughts but actually increases the occurrence and persistence of distressing thoughts. Embodiments of the system and method not only take into account the fact that "thought suppression techniques" are detrimental; they also eliminate the negative effects of "thought suppression."

13. User Smiles

The (Duchenne) smile indicates a very specific endpoint in the process. Studies have indicated that it is impossible to feel a negative mood when a person has what is known as a Duchenne Smile (a true natural smile involving muscles around the eyes). Smiling in which the muscle around the eye contracts, raising the cheeks high (Duchenne smiling) is uniquely associated with positive emotion.

D. Physical Changes

1. Physical Changes that Erase Stress

The prefrontal cortex and the amygdala are reciprocally related. In order for the amygdala to respond to fear reactions, the prefrontal region has to be shut down. When the prefrontal region is active, the amygdala would be inhibited making it harder to express fear. Pathologic fear, then, can only occur when the amygdala is unchecked by the prefrontal cortex, non-pharmaceutical treatment of pathologic fear requires a person to learn to increase activity in the prefrontal region so that the amygdala is less free to express fear. Although objective information about the world may indicate that a situation is not dangerous, because someone oppressed by an unchecked amygdala cannot properly regulate fear circuits, they experience fear and anxiety in these (objectively but not subjectively-seeming) safe situations.

When the total of inhibitory influences on the prefrontal cortex, by subcortical structures such as the amygdala, are greater than the excitatory influences, the prefrontal cortex and executive functions are "shut down," i.e., cannot occur or are substantially hindered.

It has been clearly demonstrated that stress impairs higher-order prefrontal cortex abilities such as working memory and attention regulation. Thus, attention regulation switches from thoughtful 'top-down' control by the prefrontal cortex that is based on what is most relevant to the task at hand to 'bottom-up' control by the sensory cortices, whereby the salience of the stimulus captures our attention.

Research demonstrates that exposure to even brief periods of intense stress is sufficient to cause significant structural remodeling of neurons within the prefrontal cortex. Stress-induced alterations in prefrontal cortex neuronal morphology are associated with deficits in executive functions such as working memory, attention, cognitive flexibility, and additionally cause emotional dysregulation. The molecular basis of stress-induced changes in prefrontal cortex morphology and function are only now being elucidated.

2. Activation of the Parietal Cortex Area

The parietal cortex PC (FIG. 17) is generally activated while holding the Card and doing math equations. The parietal lobe plays important roles in integrating sensory information from various parts of the body, knowledge of numbers and their relations, and in the manipulation of objects. Its function also includes processing information relating to the sense of touch. Portions of the parietal lobe are involved with visuo-spatial processing. The posterior parietal cortex is often referred to by vision scientists as the stream of vision, the "where" stream (as in spatial vision) and the "how" stream (as in vision for action). The posterior parietal cortex receives somatosensory (sense of body) and visual input, which then, through motor signals, controls movement of the arm, hand, as well as eye movements.

3. Brain Activation in Connection with Speaking

More brain activation occurs when the equations are answered out loud. However, the same areas in the brain and the same nerves which innervate the muscles of facial expression and articulation are activated to some degree whether the answers are articulated out loud or silently.

A portion of the parietal cortex is called the primary somatosensory cortex. The somatosensory cortex is the main sensory receptive area for the sense of touch. Based on the functions listed above for the parietal and somatosensory cortex, the system and method activates the cortex to an extensive degree both by physically holding the Card of the system and method, and by looking at the Card and doing the math equations. The extent of the sensory and motor brain "territory" devoted to the hand is quite impressive as seen in a famous model of the body as it would look if it was proportional to the brain territory devoted to it. Again, this fact points to the importance of a physical Card or object used in connection with the system and method.

4. Five Functions of Working Memory

Five specific functions of working memory, attention and Executive Functions taken together which are important to consider in this summary are:

1. SELECTIVE ATTENTION—what is focused on.
2. MENTAL RESOURCE ALLOCATION—which things in combination are considered.
3. DECISION MAKING—choices between options, including goal prioritization.
4. VOLUNTARY MOVEMENT—self-generated action.
5. RESOLUTION OF CONFLICTING STIMULI—handling of situational contradictions.

5. Synaptic Plasticity

Synaptic plasticity is the ability of synapses to strengthen or weaken over time, in response to increases or decreases in their activity.

Plastic change results from the alteration of the number of receptors located on a synapse. There are several underlying mechanisms that cooperate to achieve synaptic plasticity, including changes in the quantity of neurotransmitters released into a synapse and changes in how effectively cells respond to those neurotransmitters.

Synaptic plasticity occurs in cortical and sub-cortical brain structures.

Spaced practice vs. massed practice increases synaptic plasticity and improves LEARNING. Studies of behavior ranging from learning in academics, playing sports and playing a musical to forming positive or negative habits to the relative effectiveness of psychological therapy in between therapy sessions have demonstrated that "spaced" intervals consisting of many short, stretched out over time sessions are more effective than longer, concentrated in time sessions. The system and method takes this into account by its "just in time" nature. That is, not only is the use of the system and method of short duration and spaced out over time, but its use is much more closely related in time to when it is needed (i.e., when stress is veering to the uncontrollable variety).

6. Focus Control

The prefrontal cortex and the amygdala are reciprocally related. In order for the amygdala to respond to fear reactions, the prefrontal region has to be shut down. Synaptic plasticity in the prefrontal cortex as a result of increased prefrontal activity inhibits the amygdala, making it harder to express fear and the subsequent "Forced Attention" caused by the amygdala to the object of stress (the Stressor). Selective attention and selective focus of prefrontal Executive Functions could be restored if a person learns to increase activity in the prefrontal region.

7. Memory Improvement

Cortisol works with epinephrine (adrenaline) to create memories of short-term emotional events; this is the proposed mechanism for storage of flash bulb memories[44] and may originate as a means to remember what to avoid in the future. However, long-term exposure to cortisol damages cells in the hippocampus; this damage results in impaired learning. Furthermore, it has been shown that cortisol inhibits memory retrieval of already stored information.

[44] A flashbulb memory is a memory that was laid down in great detail during a personally significant event, often a shocking event of national or international importance. These memories are perceived to have a "photographic" quality. The term was coined by Brown and Kulik (1977), who found highly emotional memories (e.g. hearing bad news) were often vividly recalled, even sometime after the event. For example, a great many people can remember where they were when they heard of the terrorist attacks on Sep. 11, 2001 or the assassination of U.S. President John F. Kennedy, civil rights leader Martin Luther King Jr., or musician John Lennon.

Attenuating the unavoidable stress responses which occur throughout the day and day to day by virtue of quickly using the system and method, decreases chronic stress resulting in a decrease in excessive glucocorticoids[45] (cortisol).

[45] Glucocorticoids . . . steroid hormones that are synthesized by the adrenal cortex of vertebrates and have anti-inflammatory activity

8. Altering CRH Amounts Or Flow

In response to the initial fear-signaling impulses generated by the amygdala the hypothalamus releases corticotrophin releasing hormone (CRH). CRH from the hypothalamus stimulates the pituitary gland to release Adrenocorticotropic hormone (ACTH) which courses through the blood stream eventually stimulating the adrenal gland to secrete the hormone cortisol into the blood stream. CRH then is the main hormone in a very complex system which initiates the cascading conversion from the acute stress response to the chronic stress response.

9. Hippocampus Activation

The hippocampus contains high levels of glucocorticoid receptors (cortisol), which make it more vulnerable to long-term stress than most other brain areas. Stress-related steroids affect the hippocampus in at least three ways: first, by reducing the excitability of some hippocampal neurons; second, by inhibiting the genesis of new neurons; third, by causing atrophy of dendrites[46] in certain type of neuron in the hippocampus. There is evidence that humans having experienced severe, long-lasting traumatic stress show atrophy of the hippocampus more than of other parts of the brain. These effects show up in post-traumatic stress disorder, and they may contribute to the hippocampus atrophy reported in schizophrenia[47] and severe depression. A recent study has also revealed atrophy as a result of depression.

[46] Dendrite . . . is any of the short-branched threadlike extensions of a nerve cell, which conduct impulses inward towards the cell body.
[47] Schizophrenia, according to psychiatry, is a severe mental disorder characterized by some, but not necessarily all, of the following features: emotional blunting, intellectual deterioration, social isolation, disorganized speech and behavior, delusions, and hallucinations.

10. Increased Blood Flow to the Limbic Brain and the Amygdala

The amygdala is the hub of the complex system including the sympathetic nervous system, the HPA axis, various brain structures, synapses, hormones and neurotransmitters. Through these complex interactions the amygdala is essential to emotions particularly strong emotions. Built into these systems are feed forward mechanisms which basically pour gasoline on the fire. As the inventor has seen and as all humans who have experienced stress know, stress can disrupt the five functions of working memory. Working memory is the system that actively holds multiple pieces of transitory information in the brain, where they can be manipulated. Working memory is generally considered to have limited capacity. A dual-task paradigm is an experimental procedure that requires an individual to perform two tasks simultaneously. Studies have consistently demonstrated that intrusive stressful thoughts which force attention on the source of the stress (Task 1) are minimized, dissipated, interfered with and altered in very important ways by undertaking another task at the very same time (Task 2). The dual-task paradigm is an essential component of the system and method, and is utilized to both intervene in a stressful situation and immunize against later stress. Aspects of the system and method and the use of the dual task paradigm such as Math Distraction and Cognitive Reappraisal will be described below.

11. Increasing Oxytocin in the Brain

Oxytocin is secreted from the pituitary gland, and although it has many functions and there are many nuances to a thorough discussion of its functions, oxytocin can be called the Trust Hormone. CRH and oxytocin are interrelated. We will focus on one particular brain structure out of the many we could have chosen.

The trust-boosting effect of oxytocin works by reducing activity in the brain's fear center, the amygdala. Oxytocin also works by weakening the connections within the brain's fear-processing circuitry in response to fearful stimuli.

CRH is the hormone released by the hypothalamus which initiates the hormonal stress response. In the end this chemical cascade[48] makes it back to the central nucleus of the amygdala which strongly influences our thoughts and actions during stress. CRH acts on the central nucleus in a feed forward manner putting more coals on the stress fire. However, there are also feedback inhibitory neurons acting on the central nucleus of the amygdala which rein in the output of the nucleus calming things down. These inhibitory, "calming down" neurons use a very specific neurotransmitter to send their message—oxytocin! The effect of Oxytocin is circular. Release of Oxytocin in the brain calms things down and imparts in the individual feelings of trust. It is released when people are in a situation of trust, for example, when one see's one's family.

[48] A Cascade is anything that resembles a waterfall, especially in seeming to flow or fall in abundance; e.g., a consecutive sequence of chemical or physical processes.

12. Increasing Dopamine in the Brain

Dopamine, like Oxytocin, has an impressive number of functions and effects in the body and brain. For the inventor's purposes here we will look at one function—dopamine is the "Seeking Neurotransmitter". It release in the brain will facilitate seeking a reward. Once the reward is achieved (or satiated) dopamine levels drop off dramatically. This works well except in the case of addictions of all types. Dopamine and the nucleus accumbens, (a key brain structure in the brain's reward circuitry) interact to not only facilitate our seeking a reward but to make the activity rewarding in the first place.

13. Neutralizing Demand Exaggeration

Use of the system and method activates prefrontal circuits and dampens the impact of the stress response on prefrontal circuits. Once the initial physiologic stress response is attenuated the Executive Functions of the prefrontal circuits allow us to see that rewards are possible.

14. Erasing Compulsive Copying

A mirror neuron is a neuron that fires both when an animal acts and when the animal observes the same action performed by another. Thus, the neuron "mirrors" the behavior of the other, as though the observer were itself acting. In humans, brain activity consistent with that of mirror neurons has been found in the premotor cortex[49], the supplementary motor area[50], the primary somatosensory cortex[51] and the inferior parietal cortex[52].

[49] The Premotor Cortex is responsible for sensory guidance of movement and control of muscles.

[50] Supplementary Motor Area (SMA) is just in front of the primary motor cortex. The SMA is implicated in the planning of motor actions and is associated with bimanual (using or requiring both hands) control. One could say that the SMA sends a "plan" of the motor action to the primary motor cortex, which executes the action. The SMA is implicated in actions that are under internal control, such as the performance of a sequence of movements from memory (as opposed to movements guided by a visual cue).

[51] The Primary Somatosensory Cortex is formed by two hemispheres that receive information from the opposite (contralateral) side of the body. For example, the right primary somatosensory cortex receives information from the left limbs, and the right visual cortex receives information from the left visual field. The organization of sensory maps in the cortex reflects that of the corresponding sensing organ, in what is known as a topographic map. Neighboring points in the primary visual cortex, for example, correspond to neighboring points in the retina.

[52] The Inferior Parietal Cortex lies at a key location in the brain, at the junction of the auditory, visual, and somatosensory cortexes, with which it is massively connected. In addition, the neurons in this lobule (subdivision of a lobe) can process different kinds of stimuli (auditory, visual, sensorimotor, etc.) simultaneously. This combination of traits makes the inferior parietal lobule an ideal candidate for apprehending the multiple properties of spoken and written words: their sound, their appearance, their function, etc. This lobule may thus help the brain to classify and label things, which is a prerequisite for forming concepts and thinking abstractly.

Mirror neuron systems in the human brain help us understand the action and intentions of other people. Mirror neurons help us discern if another person who was picking up a cup of tea planned to drink from it or clear it from the table. In addition, mirror neurons may be the neural basis of the human capacity for emotions such as empathy.

During a stressful event, automatic imitation is subject to input modulation by attentional processes, and output modulation by inhibitory processes. It is mediated by learned, long-term sensorimotor associations that cannot be altered directly by intentional processes. Many researchers believe that automatic imitation is mediated by the mirror neuron system.

One of the system and method's one-of-a-kind attributes is that using it as directed under its "When" and "How" instructions increases the occurrence of synaptic pathway/circuit expansion within the brain of the user, starting at ages ranging from "pre-teen attribute all the way through to 90+". Synaptic Pathway/Circuit Expansion is a tangible way to describe increase in wisdom and intelligence.

A mirror neuron is a neuron that fires (copying) both when an individual acts and when the individual observes the same action performed by another.

15. Undoing Single Factor Obsession

The simplest directive of the stress circuits from its earliest initiation, designated above as the "low road," is to pay undivided attention to that uncertainty, threat or danger in one's environment. This "Forced Attention" or "Single Factor Obsession" has throughout eons of time been an extremely successful evolutionary mechanism to keep humans and other mammals alive. Volumes have been written about the fact that in modern times, at least for humans, this hard wired alarm system causes us many problems.

The system and method utilizes the concept of selective attention, attention determined by personal choice and motivation, to counteract this very powerful attentional redirection. But, this ability of self determination must be incrementally, plastically, built back into our brains while we are under stress. In addition to all of the other scientific reasons the system and method is effective, the "How To" and "When To" protocol maximizes this ability.

16. Eliminating Decision-Factor Rejection

Depending on the Stressor and the decision or decisions to be made the amygdala and its allies inhibit our ability to make conscious decisions. The system and method utilizes small decisions made over and over from the time someone decides to use the Card, decides which side to use, decides for example what "3×2" equals, to deciding they are finished because they achieved a (Duchenne) smile, to overcome "decision rejection." This aspect of the system and method, small decisions made over and over again, activate Executive Functions of the prefrontal cortex.

17. Re-Engaging the Self Correcting Functions of the Brain

The PFC is the prefrontal cortex. The prefrontal cortex (PFC) is the most anterior part of the frontal lobes of the brain. This brain region is responsible for planning complex cognitive behavior, (of course, consciously), "personality" expression, decision making, and moderating social behavior. The basic activity of this brain region is considered to be orchestration of thoughts and actions in accordance with internal goals. The prefrontal cortex is highly interconnected with much of the brain, including extensive connections with other cortical, sub-cortical and brain stem sites. The prefrontal cortex is especially interconnected with brain regions involved with attention, cognition and action and it also interconnects with brain regions involved with emotion.

The "ACC" is the Anterior Cingulate Cortex. The ACC is an area of the cortex which connects the sub-cortical structures such as the amygdala, basal ganglia[53] and others to the prefrontal cortex. The ACC has many functions but important to this summary is that it detects and monitors errors, evaluates the degree of the error, and then suggests an appropriate form of action to be implemented by the motor system. Studies indicate that the ACC "picks up" errors when the emotional and cognitive aspects of a given situation are incongruent.

[53] Basal Ganglia . . . Mammalian basal ganglia are nerve bundles associated with a variety of functions: motor control, cognition, emotions, and learning.

Plastic changes (see above) in the brain based on learning and memory result in an increase in the relative strength of Prefrontal circuits through consistent use of the system and method. The plastic changes are not limited to a particular brain structure. Instead, plastic changes occur throughout the entire brain, in this case throughout the prefrontal circuits, anterior cingulate cortex and sub-cortical structures.

18. Erasing Involuntary Actions

Working memory is negatively affected by stress. When the stress circuits dominate, the inverse of the five prefrontal functions exists for the individual as listed below:
 1. Selective Attention becomes—"Forced Attention"
 2. Mental Resource Allocation becomes—"Resource Blindness" or "Single Factor Obsession"
 3. Decision Making becomes—"Status Quo Bias" or "Decision Rejection"
 4. Voluntary Movement becomes—"Involuntary Stress-Driven Movements"
 5. Resolution Of Conflicting Stimuli becomes—"Unresolved(ing) Conflicts"

Depending on the stressor, the involuntary movement erased is whatever action the amygdala and its allies were forcing on consciousness.

As an example of yet another way the system and method breaks up the real life manifestations of stress . . . Studies have demonstrated that stress-produced motion tends to be bilateral, right and left hands move synchronously, simply picking up a Card of the system and method with one hand breaks this physical motion cycle. On a more grand scale most of us can recall relatively complicated actions we have carried out while under stress and only after later reflection realize we did anything!

Figure 19:
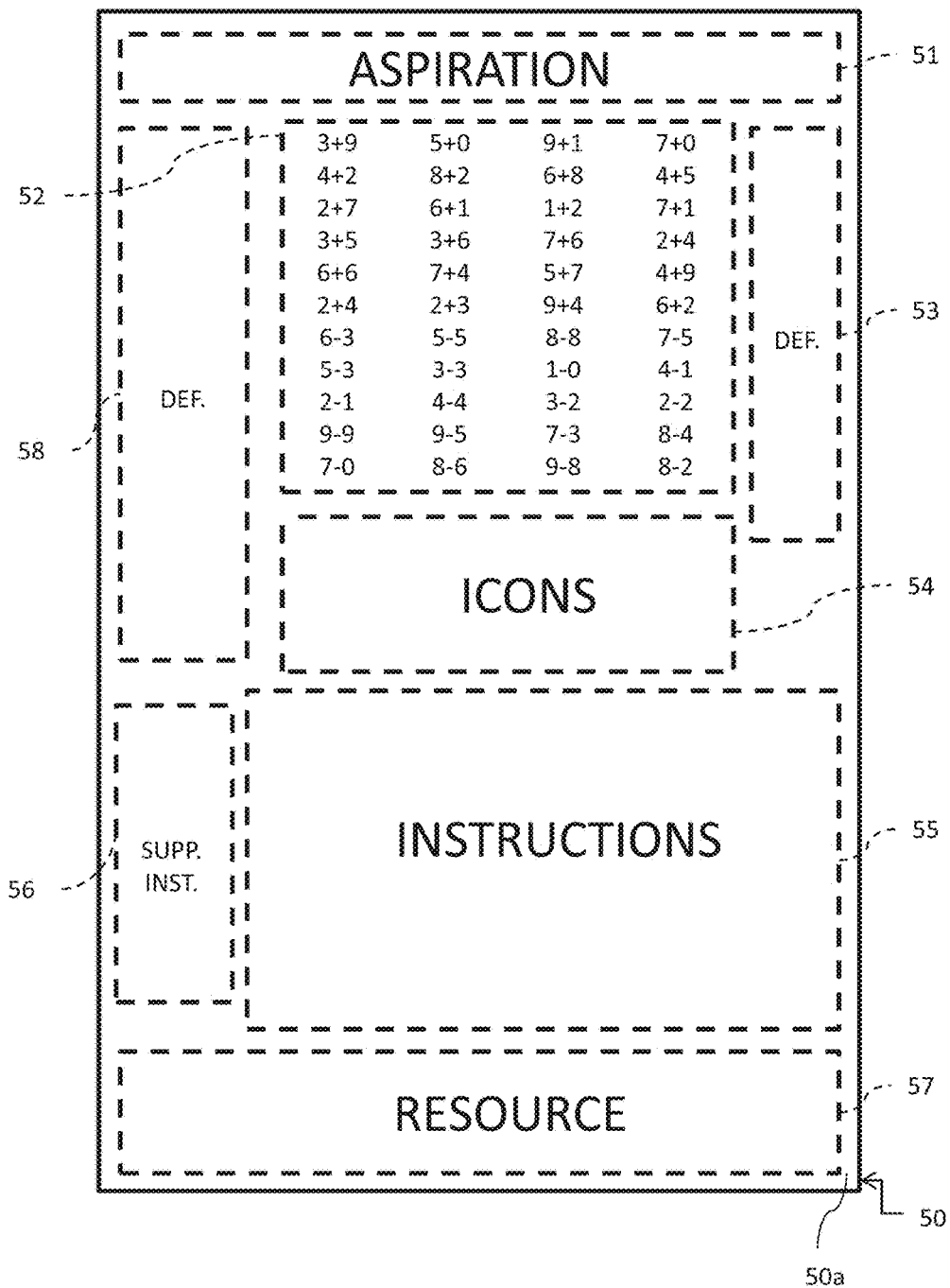
FIGS. 19-20 show front and back, respectively, of another embodiment of the Card.
Figure 20:
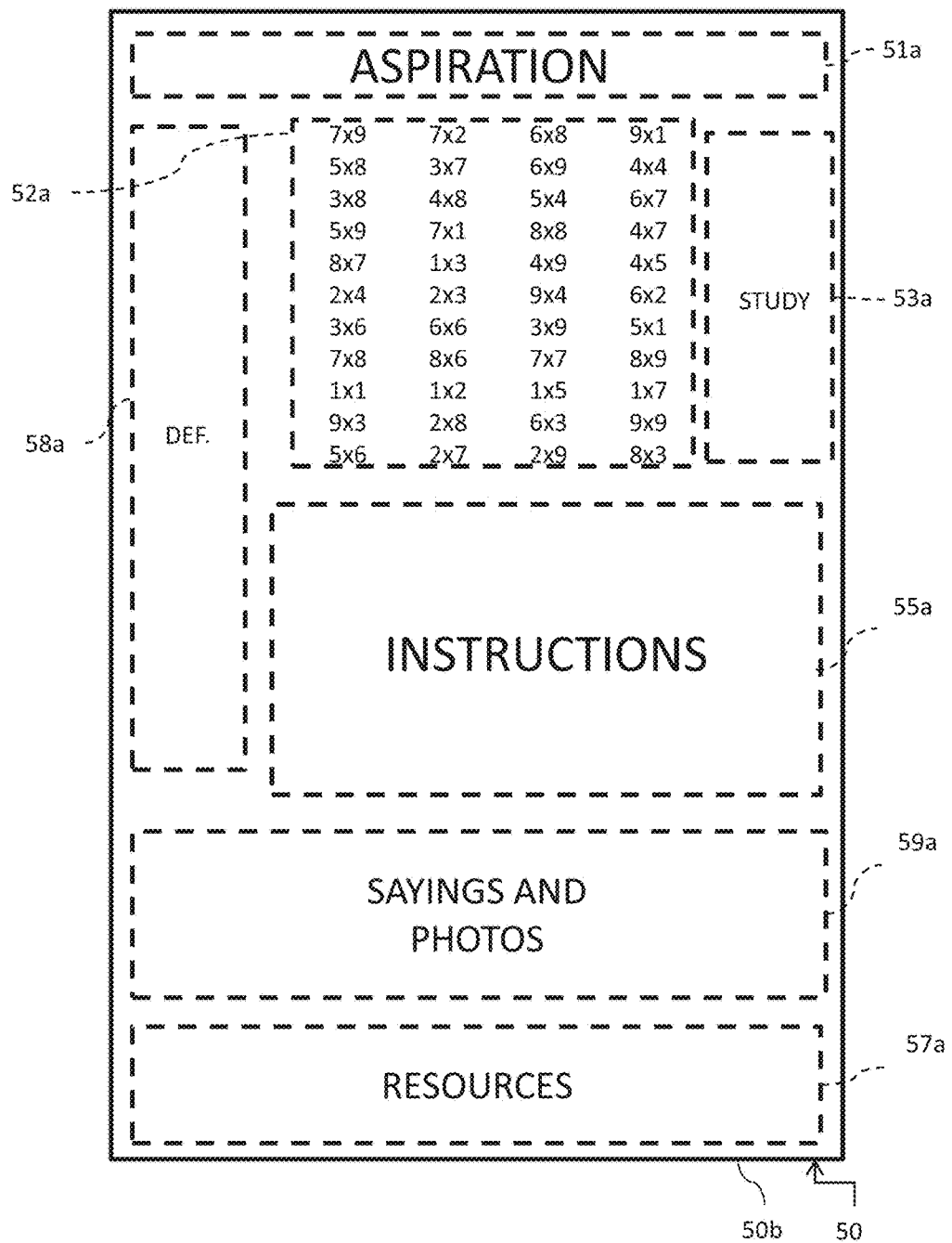

FIGS. 19-20 show front and back, respectively, of another embodiment of the Card. In this embodiment, the front and back of the Card show the motivational phrase "Become An Expert On Being Yourself" and indicates that the Card helps or can help with handling whatever is next no matter what. The front and back contain the same type of mathematical problems and the same instructions or substantially the same instructions as the prior embodiments.

FIGS. 19-20 shows a Card (front and back, respectively) like that of FIGS. 1 and 2, and/or FIG. 15, but of a different embodiment. In this embodiment, Card 50 has a front side 50a with a math problem section 52 containing rows and/or columns of math problems, e.g., having single digit addition problems (but as in any embodiment, the problems may be single digit addition, subtraction and/or multiplication). The Card may also have a Section 51 containing an aspirational phrase or phrases such as:

Become An Expert On Being Yourself
TO HANDLE WHATEVER IS NEXT NO MATTER WHAT!

The Card may have one or more "educational" or "definition" sections on one edge or part, e.g.:

Section 58 may say contain the definition: "THE OPPOSITE OF STRESS Is Trust. TRUSTING Yourself and Inspiring TRUST In Others . . . STARTS HERE!!!"

Section 53 may say:
HAPPINESS REQUIRES . . . 1. Desired Rewards Seem Possible & in View; 2. No Negative Emotions; 3. Things (Right Now) Make Sense.

There is an instructions section 55 which may say:
When to Use The TRUSTCard® . . .
1 . . . 3× Every Day: At Times You Are Not Under Stress.
2 . . . Any Other Moment You Realize You Are Under Stress.
3 . . . When Possible Before Deciding Anything Important!
4 . . . 1st Thing After Waking; Last Thing Before Bedtime.
5 . . . At Moments of Recurring Fear, Worry, Upset or Dread!

In Section 54 and elsewhere, pictures, phone numbers, copyright notice and other sayings may appear on the Card. Phone numbers and/or internet web addresses (URLs) may appear in Resource section 57. Supplemental instructions may appear in Section 56, such as:

COULD ANYTHING MAKE A DIFFERENCE? Try 1-5 The Next 7 Days!

All embodiments of the Card may have addition and subtraction problems. It may have an educational section as well, e.g., the same or substantially the same "saying" as in other embodiments. This Card may have an instructions, Stress definition and Trust definition section. The "instructions" may say:

The definition of "STRESS" and "TRUST" portions of this instructions section 55 preferably say:
STRESS DEFINED: WHEN (YOU FEEL) THE DEMANDS BEING MADE OF YOU EXCEED YOUR RESOURCES TO MEET THEM!
TRUST DEFINED: WHEN YOU (WOULD) FEEL 100% COMFORTABLE LETTING A PERSON (INCLUDING YOU) MAKE DECISIONS OR ACT ON YOUR BEHALF.

There may also be other sayings, notices, copyright notice, such as or similar to the Card of any other embodiment.

The back 50b of the Card may also have an "instructions" section 55a, which may say:
How To Use The TRUSTCard® . . .
Note: The Time (Of Day) & The Stress (Extant) & The Importance (Of An Upcoming Decision)
Then . . . Do 4 Math "Problems" Either Side.
Check For Any Stressful Feeling or Thought
Do 4 More Math "Problems" Either Side.
Check For Any Stressful Feeling or Thought
Do 4 More Math "Problems", Etc.
Check For Any STRESS AGAIN . . .
Repeat "4-Check-4" UNTIL YOU SMILE!

There may also be an Aspiration section 51a like that on the front of the Card, a definition section 58a which may say:
THE OPPOSITE OF STRESS Is TRUST. TRUSTING Yourself And Inspiring TRUST In Others . . . STARTS HERE!!!

There is a math problem section 52a, which has single digit math problems in rows and/or columns, e.g., eleven problems in each of four columns such as multiplication (addition and/or subtraction).

There may be a study section 53a indicating that "Over 90 Verified Scientific Studies Support & Explain The Principles Underlying The Efficacy Of TheTRUSTCard™."

There may also be a resources section 57a, and a section 59a with sayings and photos.

As in all embodiments of the systems and methods disclosed herein, all that is necessary on the Card are single digit math problems sufficient to carry out the process, and preferably instructions on the Card for carrying out the processes herein. Aspirational sayings, resources, graphics and other embellishments disclosed herein are not necessary to carry out the inventive processes and system herein.

Figure 21:
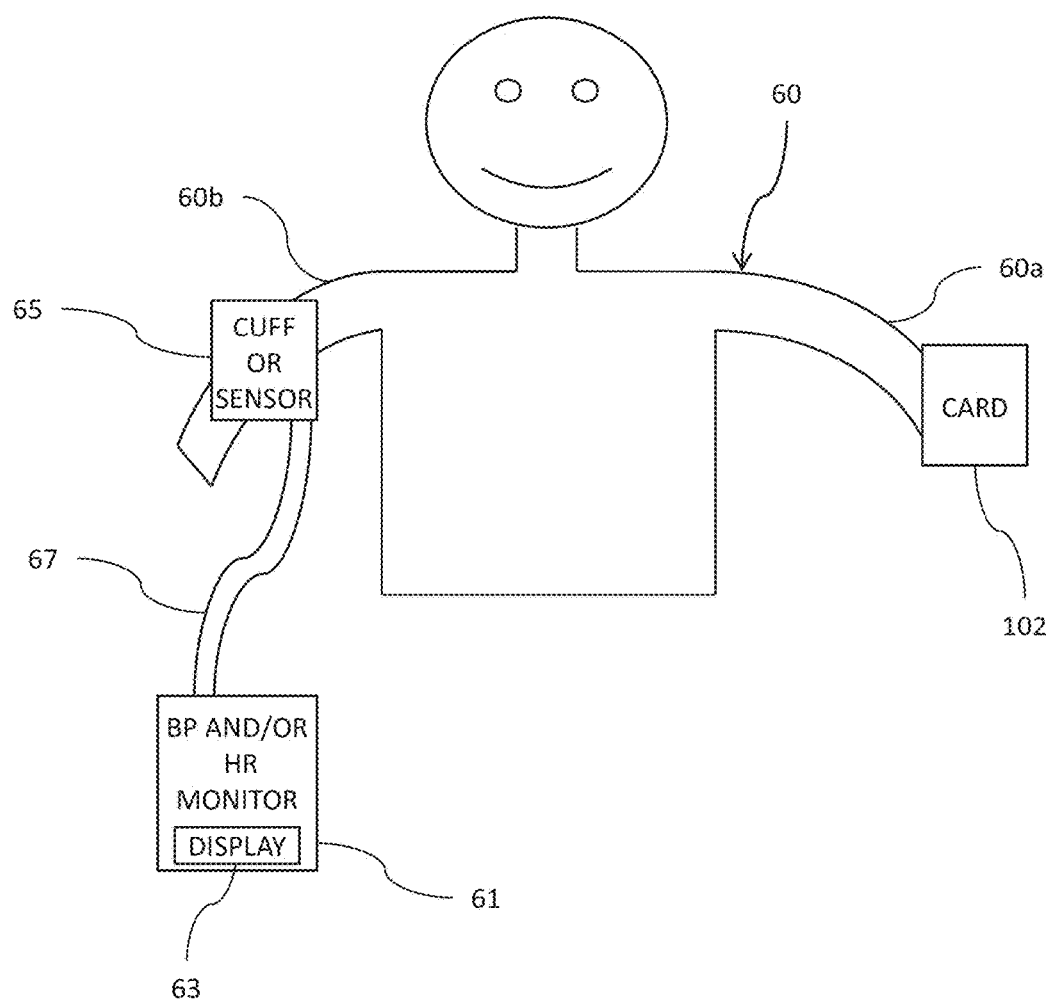
FIG. 21 shows a schematic view of another embodiment wherein the user checks his/her vital signs, such as heart rate (e.g., pulse) and/or blood pressure while using the Card and/or at intervals.
Figure 22:
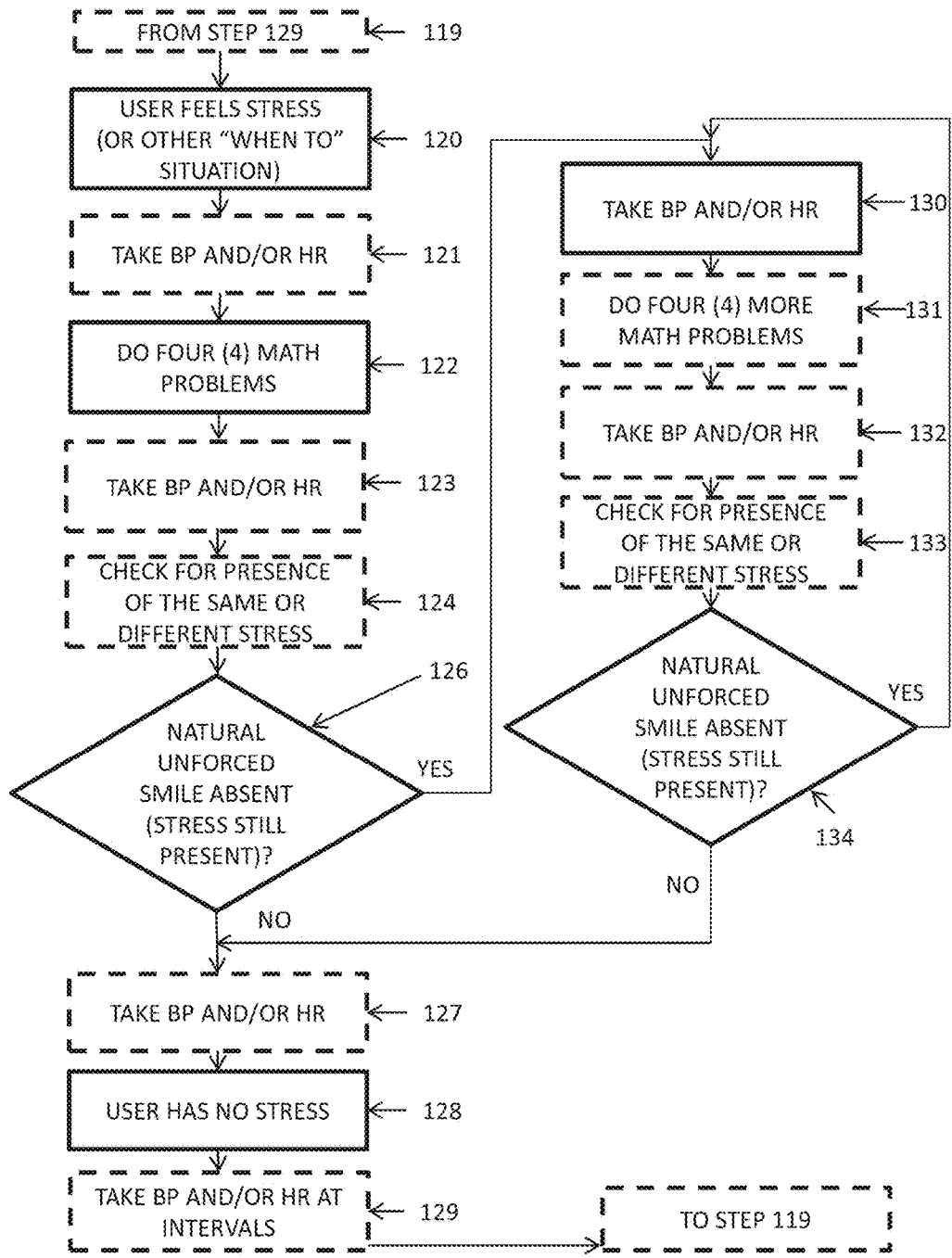
FIG. 22 is a flow chart of steps in the embodiment of FIG. 21.

FIGS. 21 and 22 illustrate another embodiment where a mechanism for monitoring various vital signs of the user while using the Card may be implemented, such as a blood pressure monitor and/or a heart rate monitor. As shown in FIGS. 21 and 22, another embodiment is similar to that of FIG. 3 and further includes a user measuring and monitoring blood pressure (BP) and/or heart rate (HR) (aka pulse).

In one version, BP and/or HR may be measured periodically, such as once a day, every other day, three times per week, once a week, once per month, or some other interval, along with regular use of the Card per any of the embodiments herein, such as that of FIG. 3.

Alternatively, and/or in conjunction with the above, the user may integrate BP and/or HR monitoring into the steps of using the Card. As shown in FIG. 21, a user 60 may hold a Card 102 in one hand 60a and have a BP and/or HR cuff or sensor 65 on the other hand or arm 60b, as appropriate for measuring BP and/or HR. Card 102 may be the same as or substantially similar to any of the Cards of the previous embodiments herein.

A BP and/or HR Monitor device 61 having a display 63 is connected by tube 67 and/or wires as appropriate to the sensor 65.

Figure 23:
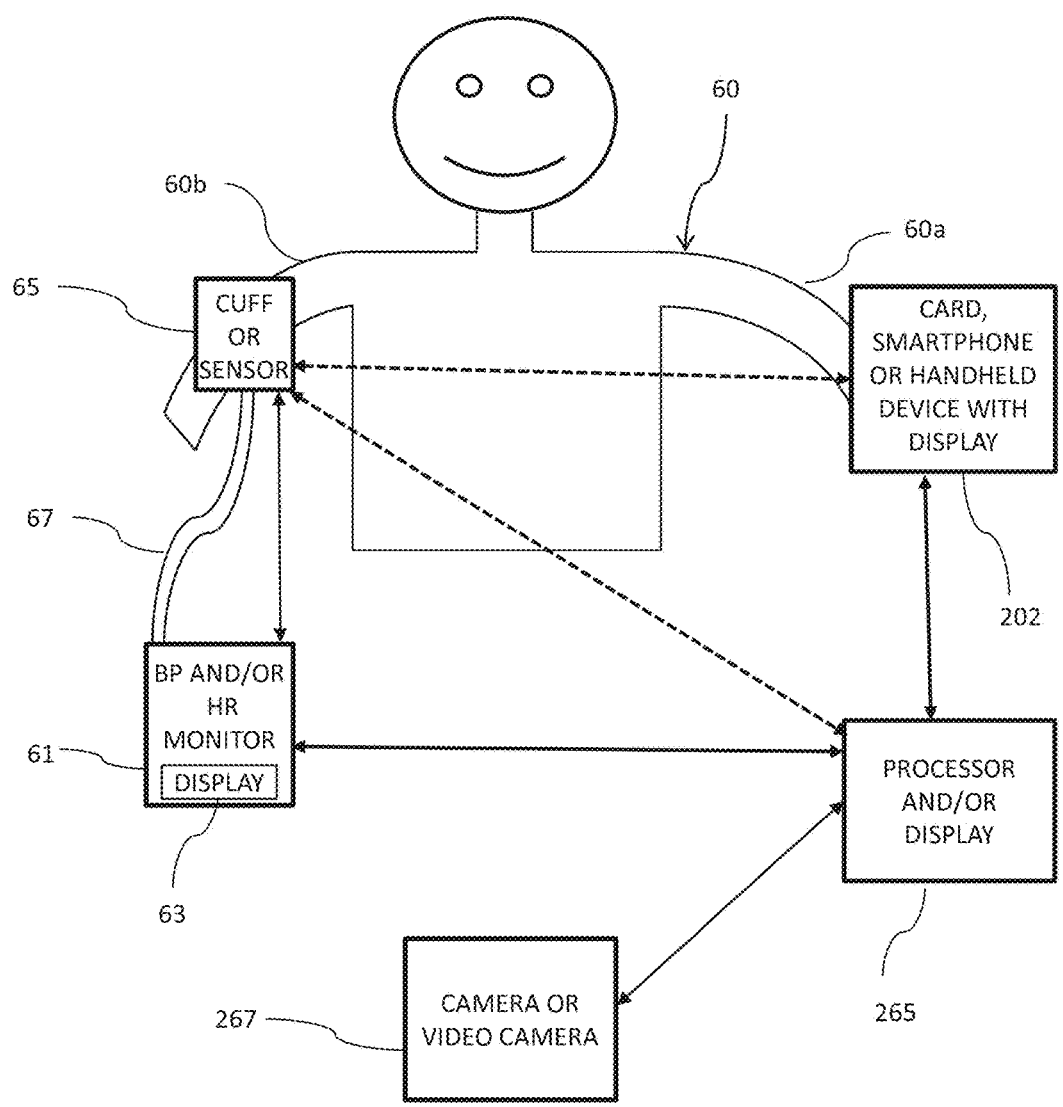
FIG. 23 is a view of a variation of the flow chart of FIG. 22 showing another embodiment of the invention.
Figure 24:
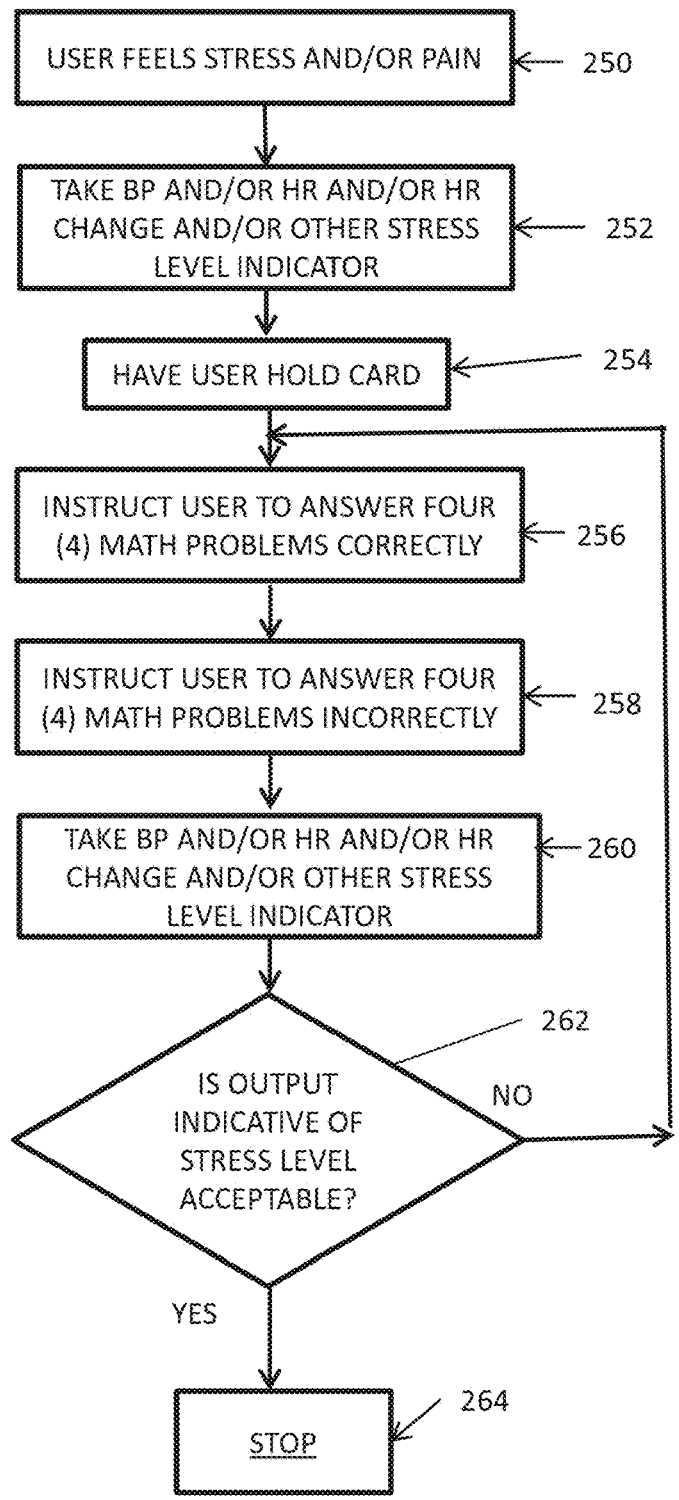
FIG. 24 is a view of another variation of the flow chart of FIG. 22 showing a further embodiment of the invention.
Figure 25:
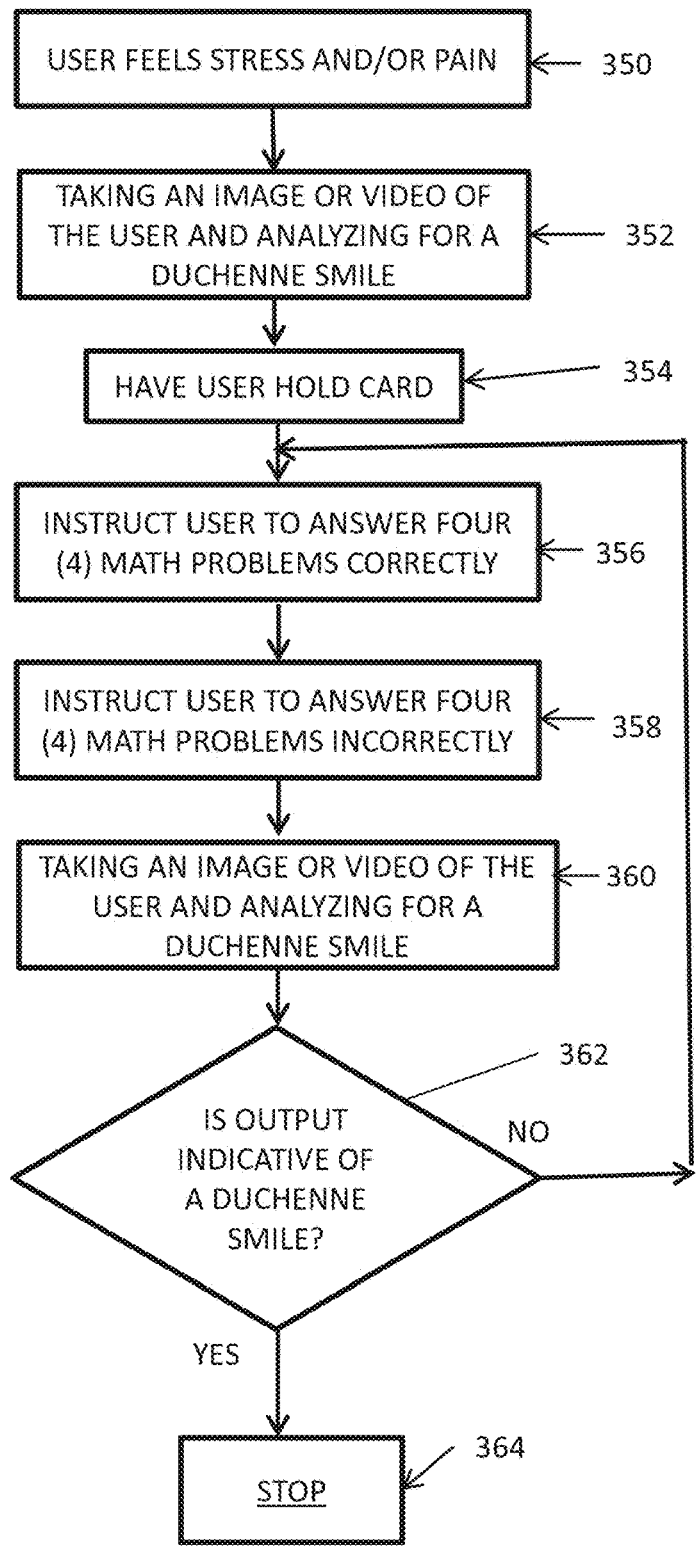
FIG. 25 is a view similar to FIG. 21, showing the variations and embodiments of FIGS. 23 and 24.

As shown in FIG. 22, the process of using Card 102 (e.g. the process of FIG. 3) may be modified by including steps of measuring BP and/or HR 121, 123, 127, 129, 130 and/or 132. The steps in the process of FIG. 3 are the same as in FIG. 3. However, in addition to, or in lieu of the steps in which the user feels or checks for the presence of stress, the user's BP or HR may be taken to determine a baseline (e.g., step 121 where the user checks BP and/or HR) prior to doing a set of four math problems (e.g., step 122), and then again after doing the math problems (e.g., at step 123). Nevertheless, the user should not stop the process until the user has a Duchenne smile. However, the BP and/or HR feedback will be helpful in enabling the user to see and monitor the progress of the process, which can itself help calm the user. In addition, when the user is done with the process (has a Duchenne smile/step 134—"no" and step 128), the user may again take BP and/or HR at step 127 or at step 129 which provides a "no stress" baseline which the user can compare to the next time the user feels stress, and restarts the process (step 119). FIG. 23 is a view of a variation of the flow chart of FIG. 22 showing another embodiment of the invention;

FIG. 24 is a view of another variation of the flow chart of FIG. 22 showing a further embodiment of the invention; and FIG. 25 is a view similar to FIG. 21, showing the variations and embodiments of FIGS. 23 and 24.

In the embodiment of FIG. 23, there is a stress and pain reduction method and system for a user. In this embodiment, the user may integrate BP and/or HR monitoring and/or other device to monitor stress, e.g., by monitoring heart rate change and/or by determining if the user has reached a point where he/she has a Duchenne smile (smiling, in which the corners of the mouth are raised and the cheeks are raised high-see footnote 3) into the steps of using the Card. As shown in FIG. 21, a user 60 may hold a Card 202 in one hand 60*a* and have a BP and/or HR cuff or sensor 65 on the other hand or arm 60*b*, as appropriate for measuring BP and/or HR. Card 102 may be the same as or substantially similar to any of the Cards of the previous embodiments herein, or it may be a display or smartphone, or a handheld device having a display and a processor.

A BP and/or HR Monitor device 61 having a display 63 is connected by tube 67 and/or wires as appropriate to the sensor 65, and/or wireless connection. Alternatively, or in addition thereto, the device (e.g., cuff or sensor 65 is connected by wires, direct connection (or is part of) and/or by wireless connection to a processor and display device 265, or to the card 202 where the card has a display and processor, such as if the card is a smartphone or other handheld electronic device.

The smartphone and/or handheld device may be enabled to measure heart rate and/or stress level, using e.g., an app, such as "Instant Heart Rate" and/or "Stress Check," both by Azumio, at www.Azumio.com, and/or "Instant Blood Pressure" by AuraLife, at www.instantbloodpressure.com. Another stress indicator device that may be used is one to monitor heart rate variability (HRV), for which an app, e.g., "Elite HRV." by Elite HRV, may be used.

FIG. 23 also shows a camera and/or video camera 267 which can take an image, series of images and/or video of the user's face, and use facial recognition software in the processor (whichever processor is desired, even if the processor is in the cloud and is used in connection with an app or otherwise). The facial recognition software would look for indications showing a Duchenne smile, e.g., raised corners of the mouth and high cheeks and/or contractions of the appropriate muscles to achieve the raised corners of the mouth and the high checks—see footnote 3). To improve accuracy, a baseline image or series of images of the user may be taken prior to following the inventive method.

With such structure, the stress and/or pain reduction method shown in the flow chart of FIG. 23 is preferably followed when, at step 250, the process may start when the user feels stress and/or pain, and/or otherwise wants to reduce stress and/or pain. The process includes the following steps:

(a) At step 252, a device such as device 65 (with monitor 61, if needed or without it, if another processor and display may be used or if it has an onboard or attached processor and display) is provided for measuring an initial stress level of a user at the start of the process. The user may also have previously used the device to take baseline stress levels. The processor, such as processor 265, may even be accessed over the internet or it may be local to the user, and may be in monitor 61, or it may be in the card 202, where the card is a handheld electronic device or smartphone. The stress level output is preferably stored, as are all outputs, in a memory, which is preferably associated with and/or part of the processor.

(b) At step 252, the user's BP and/or HR and/or rate of change of HR is taken and the monitor provides an output indicative of an initial level of stress of the user. This initial level of stress is unacceptable. The output is transmitted to the processor which displays the output on a display. The processor, as noted above, may be onboard or attached to the sensor, or it may be separate from the sensor.

(c) At step 254, the user is instructed to hold the card which has and displays multiple single digit math problems therein or thereon, of the type discussed hereinabove, i.e., addition, subtraction, and multiplication problems (single digit type).

(d) At step 256, the user is instructed to complete a first series of four and only four of the problems, and in completing the first series of problems to try to answer the problems correctly. It does not, however, matter whether the user gets the right answer or not.

(e) At step 258, the user is then instructed to view the problems on the card and to complete a second series of four and only four of the problems, and in completing the second series of problems to try to answer the problems incorrectly. Again, it does not matter, whether or not the user actually gets the wrong answer or not.

(f) At step 260, the system then measures the output from the monitoring device indicative of a level of stress of the user and transmits the output to the processor which displays the output on the display.

(g) At step 262, the processor will determine if the user's stress level has dropped the predetermined amount or has achieved the predetermined amount, and if so, then the process stops at step 264. If not, the process returns to step 256 and continues on through steps 256, 258, 260 and 262 again, until obtaining a "Yes" answer at step 262.

As shown in FIG. 25, the same steps as in the above process may be followed, except to measure success (to stop the process), may occur when a Duchenne smile is detected by the processor. The process may start at step 350, which is the same as step 250.

(a) At step 352, the camera and/or video camera takes an image or images or video of the user's face and stores that image. A baseline image, or images or video may previously have been taken.

(b) In addition, the image data is output to a processor for analyzing it, and may look for a Duchenne smile or at least store sufficient data to look for a Duchenne smile, which Duchenne smile would not typically be present at this time.

(c) At step 354, the user is instructed to hold the card which has and displays multiple single digit math problems therein or thereon, of the type discussed hereinabove, i.e., addition, subtraction, and multiplication problems (single digit type).

(d) At step 356, the user is instructed to complete a first series of four and only four of the problems, and in completing the first series of problems to try to answer the problems correctly. It does not, however, matter whether the user gets the right answer or not.

(e) At step 358, the user is then instructed to view the problems on the card and to complete a second series of four and only four of the problems, and in completing the second series of problems to try to answer the problems incorrectly. Again, it does not matter, whether or not the user actually gets the wrong answer or not.

(f) At steps 360 and 362, using the camera and/or video, an image or images and/or video is taken, and output to the processor, which analyzes the output to determine if the user has a Duchenne smile, and provides a signal indicative of whether or not the user has a Duchenne smile, and displays whether or not the user has a Duchenne smile on a display.

(g) At step 362, if the user does have a Duchenne smile, then the process stops at step 364. If the user does not have a Duchenne smile, then the user repeats steps 356 to 360 until the signal from the processor indicates that the user has a Duchenne smile.

Lastly, the processes of FIGS. 24 and 25 may be combined, by measuring by the stress indicator and by taking the image(s) and/or video, and stopping the process when either stress has dropped by or to a predetermined amount, or when a Duchenne smile is determined to exist, or requiring both to stop the process.

Although the invention has been described using specific terms, devices, and/or methods, such description is for illustrative purposes of the preferred embodiment(s) only. Changes may be made to the preferred embodiment(s) by those of ordinary skill in the art without departing from the scope of the present invention, which is set forth in the following claims. In addition, it should be understood that aspects of the preferred embodiment(s) generally may be interchanged in whole or in part.

What is claimed is:

1. A stress and pain reduction method for a user, comprising:
   (a) providing a device for viewing and analyzing a user's face, the device taking an image of the user's face;
   (b) connecting an output from the device to a processor for analyzing the image for a Duchenne smile;
   (c) having a user hold a card having multiple single digit math problems therein, the problems being in multiple series of four problems, the math problems comprising at least one of addition, subtraction, and multiplication problems, and displaying the problems to the user;
   (d) instructing the user to view the problems on the card and to complete a first series of four and only four of the problems, and in completing the first series of problems to try to answer the problems correctly;
   (e) instructing the user to view the problems on the card and to complete a second series of four and only four of the problems, and in completing the second series of problems to try to answer the problems incorrectly;
   (f) using the processor, analyzing the output from the device to determine if the user has a Duchenne smile, and providing a signal indicative of whether or not the user has a Duchenne smile, and displaying whether or not the user has a Duchenne smile on a display; and
   (g) repeating steps (d) to (f) until the signal from the processor indicates that the user has a Duchenne smile.

2. The method of claim 1, wherein the card is a smart card that includes the display device and the processor.

3. The method of claim 2, wherein the card comprises a smart phone that includes the processor and the display device.

4. The method of claim 1, wherein the device comprises at least one of a camera and a video camera.

5. The method of claim 1, further comprising the steps of providing a stress measuring device for measuring stress level of the user, and outputting an indicator output indicative of an initial level of stress of the user, which initial level of stress is unacceptable, and transmitting that output to the processor which displays the output on the display, and in step (f), again measuring the output from the device indicative of a level of stress of the user and transmitting the output to the processor which displays the output on the display.

6. The method of claim 1, wherein the math problems which the user is instructed to do are single digit math problems.

7. A stress and pain reduction method for a user, comprising:
   (a) providing a device for viewing and analyzing a user's face, the device taking an image of the user's face, and for measuring stress level of a user;
   (b) connecting an output from the device to a processor for analyzing the image for a Duchenne smile and for analyzing an output from the device for a stress level of the user;
   (c) having a user hold a card having multiple single digit math problems therein, the problems being in multiple series of four problems, the math problems comprising at least one of addition, subtraction, and multiplication problems, and displaying the problems to the user;
   (d) instructing the user, via the display, to view the problems on the card and to complete a first series of four and only four of the problems, and in completing the first series of problems to try to answer the problems correctly;
   (e) instructing the user to view the problems on the card and to complete a second series of four and only four of the problems, and in completing the second series of problems to try to answer the problems incorrectly;
   (f) using the processor, analyzing the output from the device to determine if the user has a Duchenne smile, and providing a signal indicative of whether or not the user has a Duchenne smile, and displaying whether or not the user has a Duchenne smile on a display, and again measuring the output from the device indicative of a level of stress of the user and transmitting the output to the processor which displays the output on the display; and
   (g) repeating steps (d) to (f) until the signal from the processor indicates that the user has at least one of the user having a Duchenne smile and the user having a predetermined acceptable level of stress as determined by the processor, and displaying on the display at least one of an indication that the Duchenne smile has been achieved and that the predetermined acceptable level of stress has been attained, respectively.

8. The method of claim 7, wherein the card is a smart card that includes the display device and the processor.

9. The method of claim 8, wherein the card comprises a smart phone that includes the processor and the display device.

10. The method of claim 7, wherein the device comprises at least one of a camera and a video camera.

11. The method of claim 7, wherein the math problems which the user is instructed to do are single digit math problems.

* * * * *